(12) United States Patent
Husar

(10) Patent No.: US 7,005,109 B2
(45) Date of Patent: Feb. 28, 2006

(54) SYSTEM FOR HANDLING LIQUID SAMPLES

(75) Inventor: Dieter Husar, Hamburg (DE)

(73) Assignee: Eppendorf AG, Hamburg (DE)

( * ) Notice: Subject to any disclaimer, the term of this patent is extended or adjusted under 35 U.S.C. 154(b) by 412 days.

(21) Appl. No.: 10/046,522

(22) Filed: Jan. 14, 2002

(65) Prior Publication Data

US 2002/0061260 A1      May 23, 2002

Related U.S. Application Data

(63) Continuation of application No. PCT/EP00/06213, filed on Jul. 4, 2000.

(30) Foreign Application Priority Data

Jul. 15, 1999    (DE)   ................................ 199 33 458

(51) Int. Cl.
    *B01L 3/00*   (2006.01)
(52) U.S. Cl. ...................... 422/99; 422/102; 435/288.5
(58) Field of Classification Search .................. 422/99, 422/102–104; 435/288.5, 287.1, 305.2–305.4
    See application file for complete search history.

(56) References Cited

U.S. PATENT DOCUMENTS

| | | | |
|---|---|---|---|
| 3,620,676 A | 11/1971 | David | |
| 3,799,742 A | 3/1974 | Coleman | |
| 4,077,845 A * | 3/1978 | Johnson | 435/33 |
| 4,508,622 A * | 4/1985 | Polaschegg et al. | 210/96.2 |
| 4,775,515 A | 10/1988 | Cottingham | |
| 5,500,187 A | 3/1996 | Deoms et al. | |
| 5,504,011 A | 4/1996 | Gavin et al. | |
| 5,744,366 A * | 4/1998 | Kricka et al. | 436/63 |
| 6,117,395 A | 9/2000 | Plough et al. | |
| 6,120,736 A | 9/2000 | Plough et al. | |
| 6,227,824 B1 * | 5/2001 | Stehr | 417/540 |
| 6,280,148 B1 | 8/2001 | Zengerle et al. | |
| 6,323,040 B1 * | 11/2001 | Raz et al. | 436/174 |
| 6,686,208 B1 | 2/2004 | Meusel et al. | |
| 2004/0166028 A1 * | 8/2004 | Husar et al. | 422/100 |

FOREIGN PATENT DOCUMENTS

| | | |
|---|---|---|
| DE | 9303483 | 2/1995 |
| DE | 9303898 | 2/1995 |
| DE | 9801523 | 6/1998 |
| EP | 0545284 | 6/1993 |
| EP | 0725267 | 8/1996 |
| EP | 0803288 | 10/1997 |
| EP | 0897750 | 2/1999 |
| EP | 0903180 | 3/1999 |

(Continued)

OTHER PUBLICATIONS

Wolfgang Ehrfeld et al., "Use Potentials for Chemical & Biological Microreactors," Chemie Ingenieur Technic, vol. 69 (1997) 931-934.

*Primary Examiner*—Lyle A. Alexander
(74) *Attorney, Agent, or Firm*—Abelman, Frayne & Schwab

(57) ABSTRACT

A system for handling liquid samples, comprising at least two superposed and interconnected planar elements between which a well for a liquid sample is formed which extends between an outwardly leading mouth to receive and/or deliver a liquid sample and an outwardly leading passage to connect the well to a displacement device for air or another gas.

54 Claims, 13 Drawing Sheets

FOREIGN PATENT DOCUMENTS

| | | |
|---|---|---|
| WO | 9600614 | 1/1996 |
| WO | 9614934 | 5/1996 |
| WO | 9704297 | 2/1997 |
| WO | 9744132 | 11/1997 |
| WO | 9805424 | 2/1998 |
| WO | 9935584 | 1/1999 |

* cited by examiner

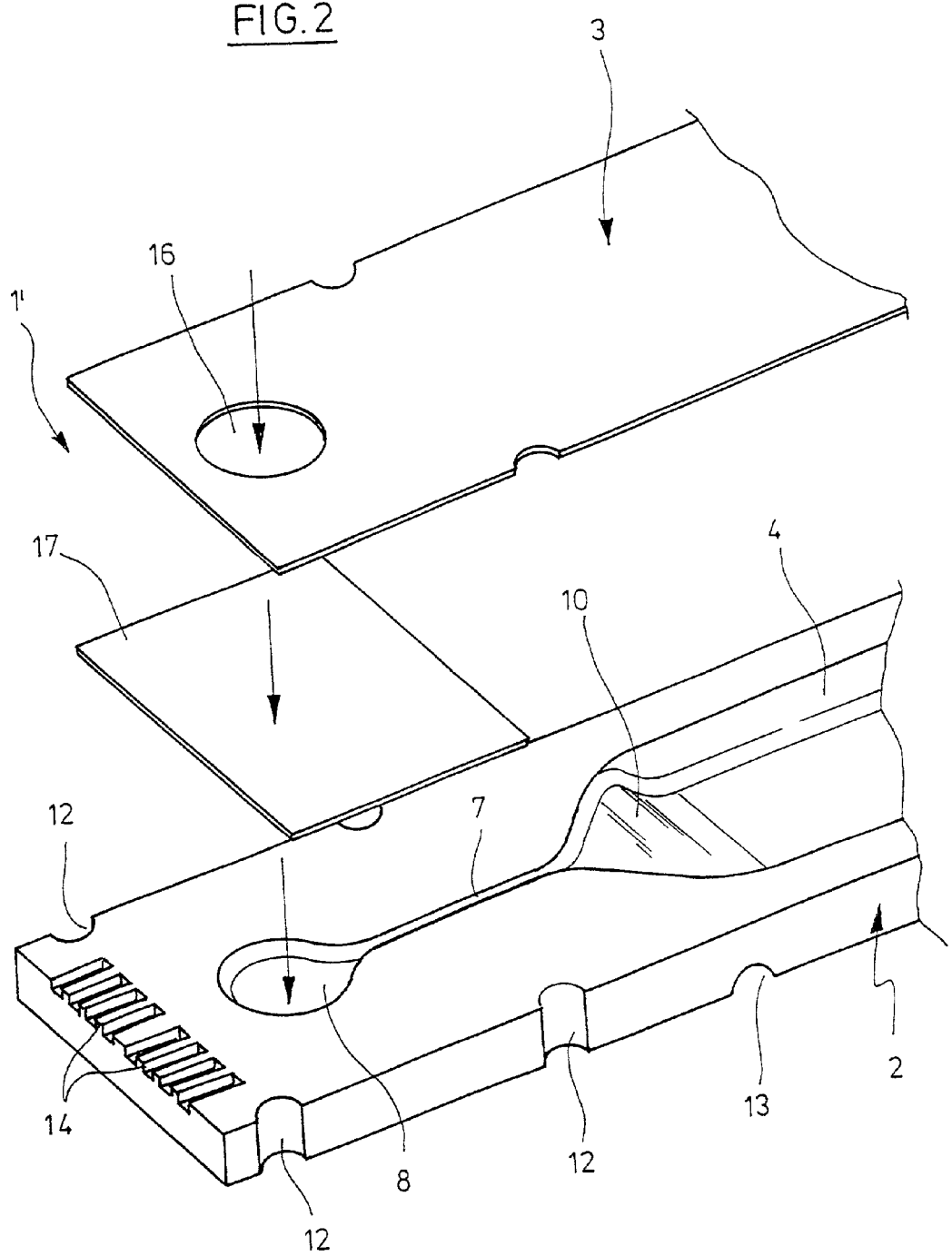

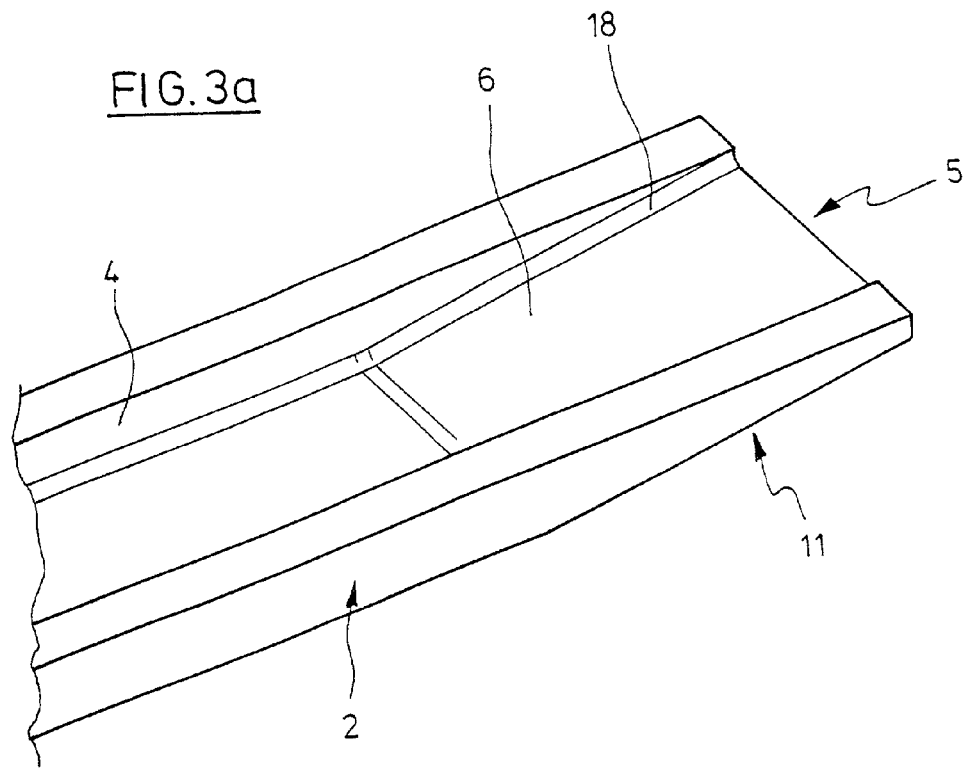
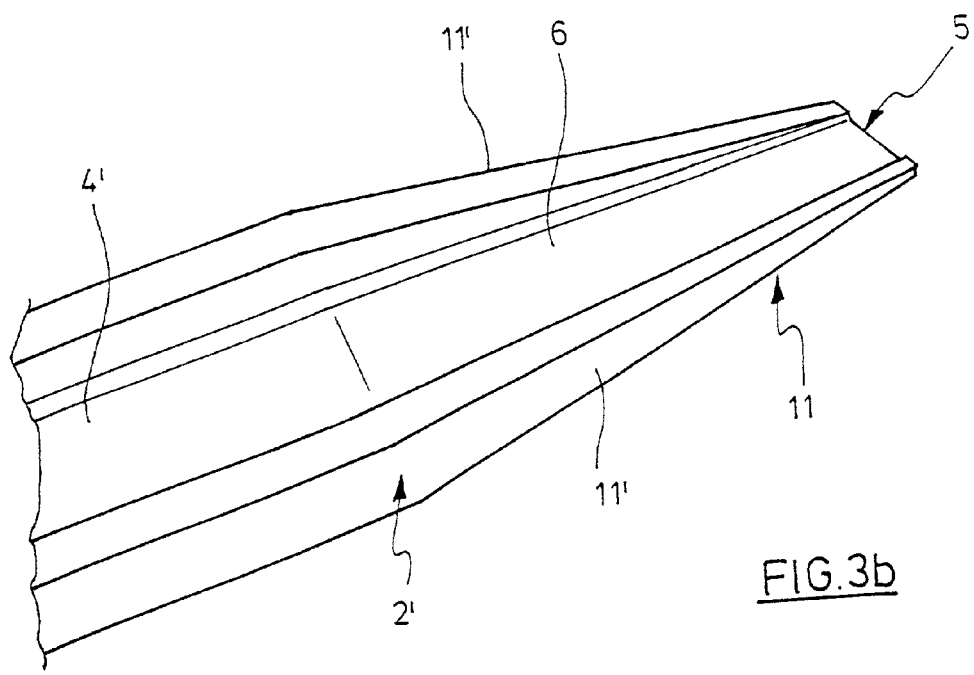

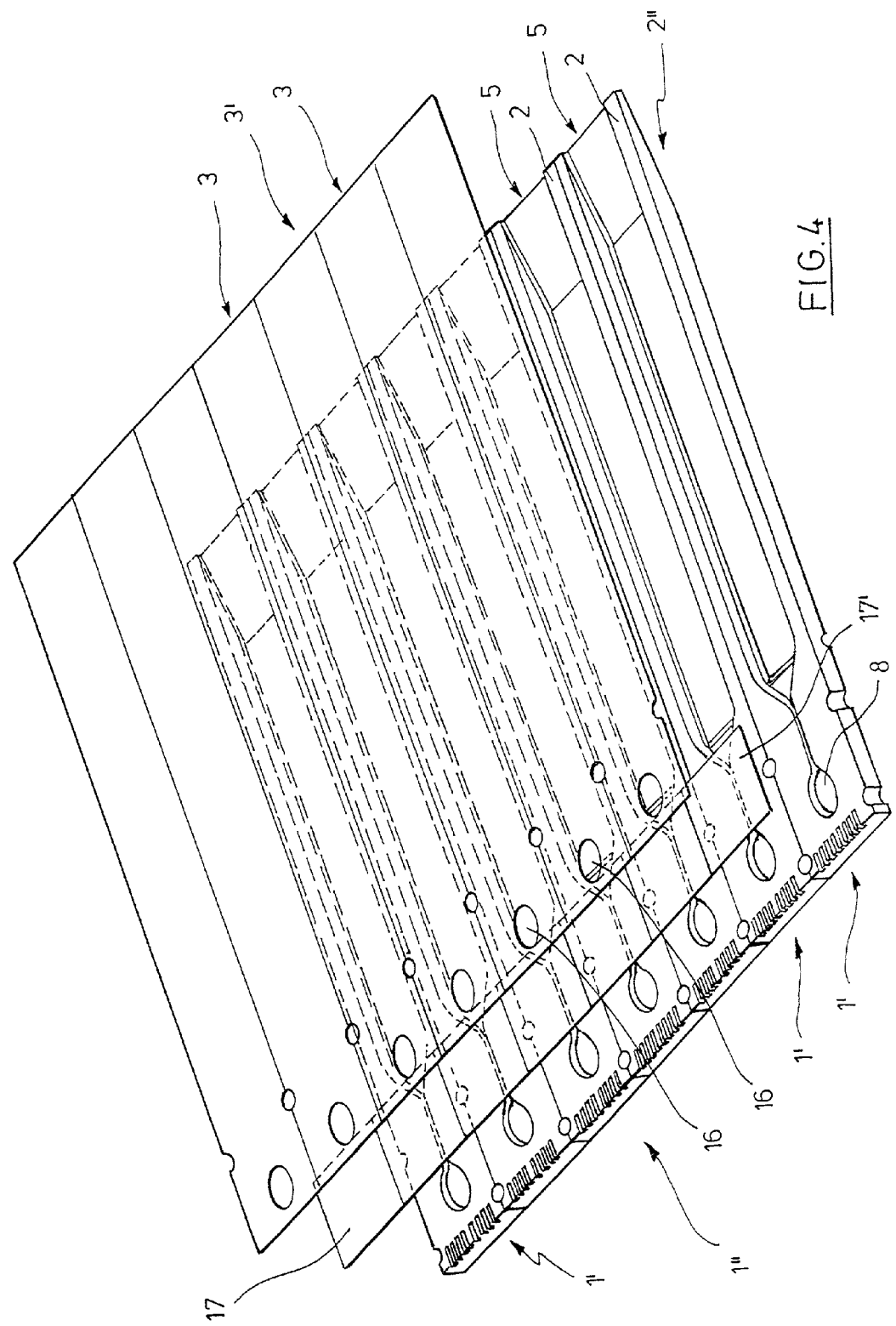

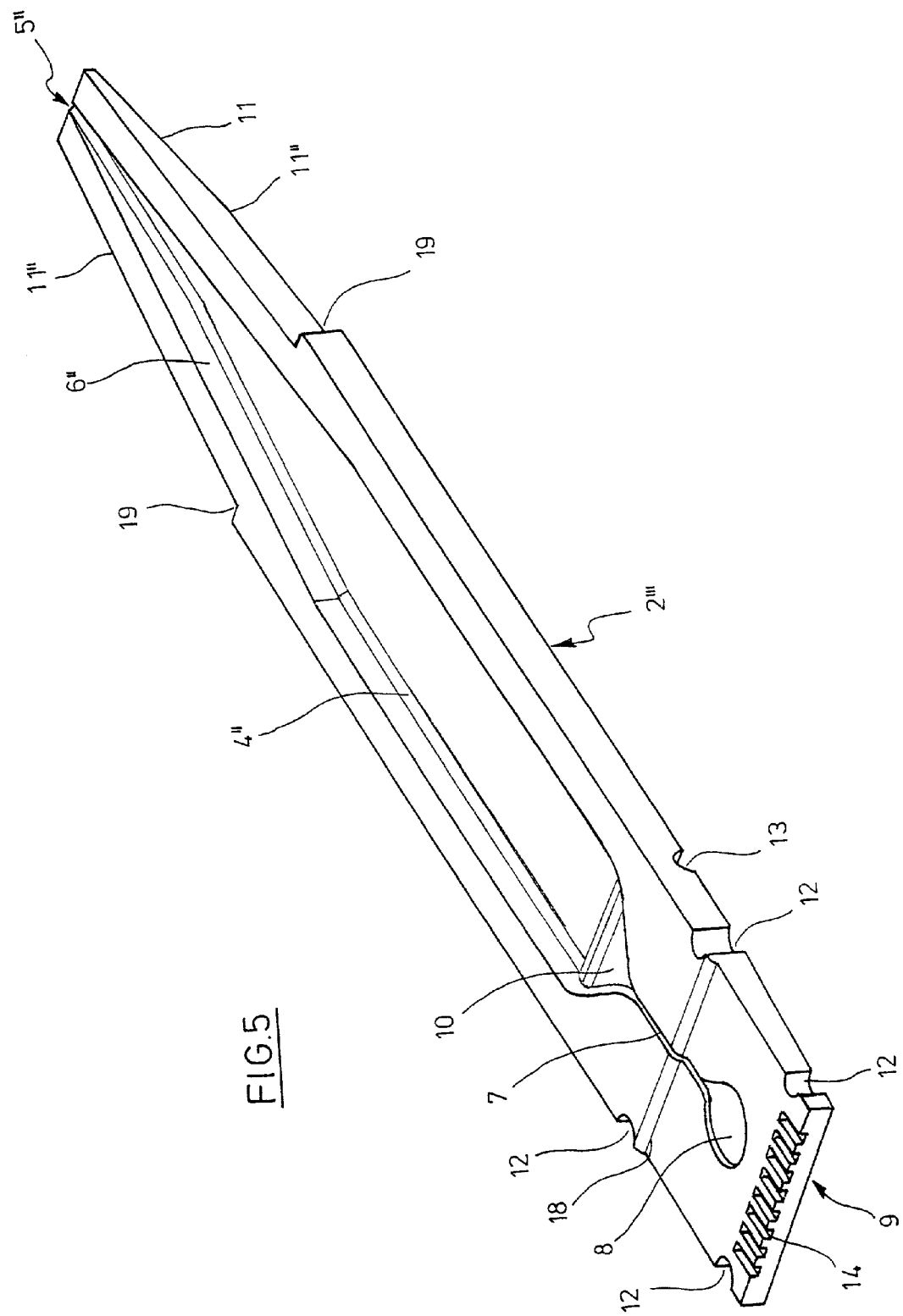

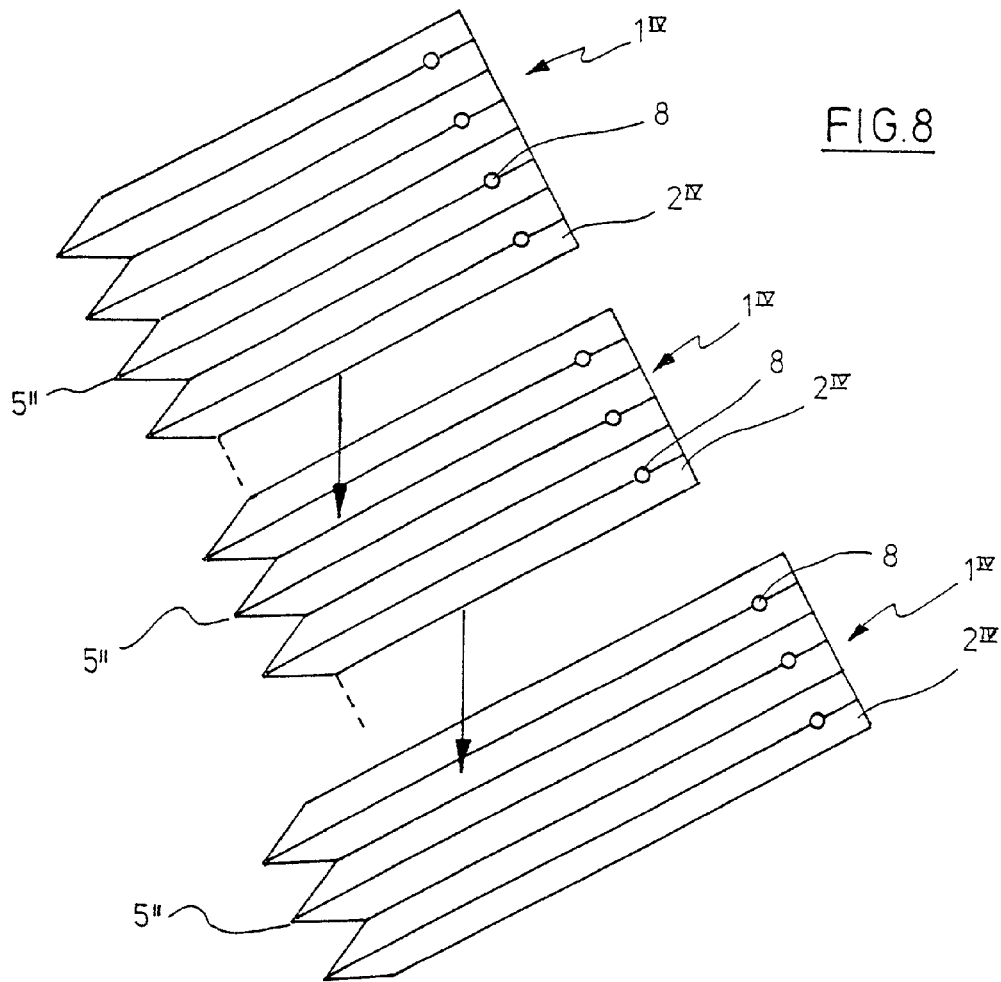
FIG.8
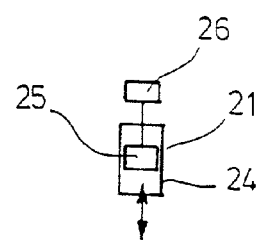
FIG.9
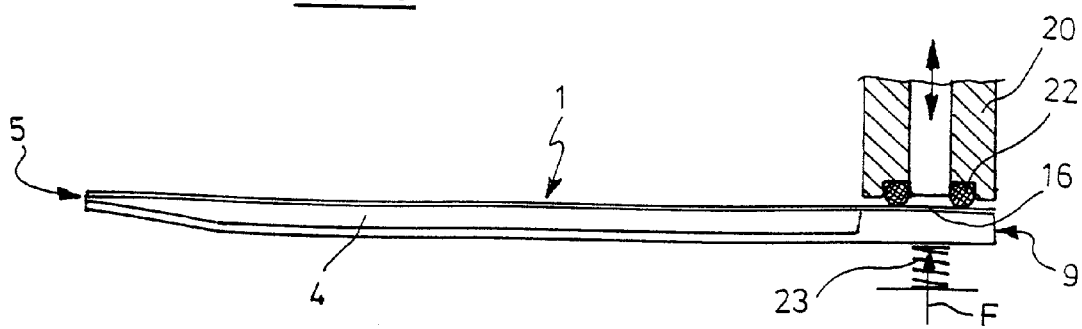

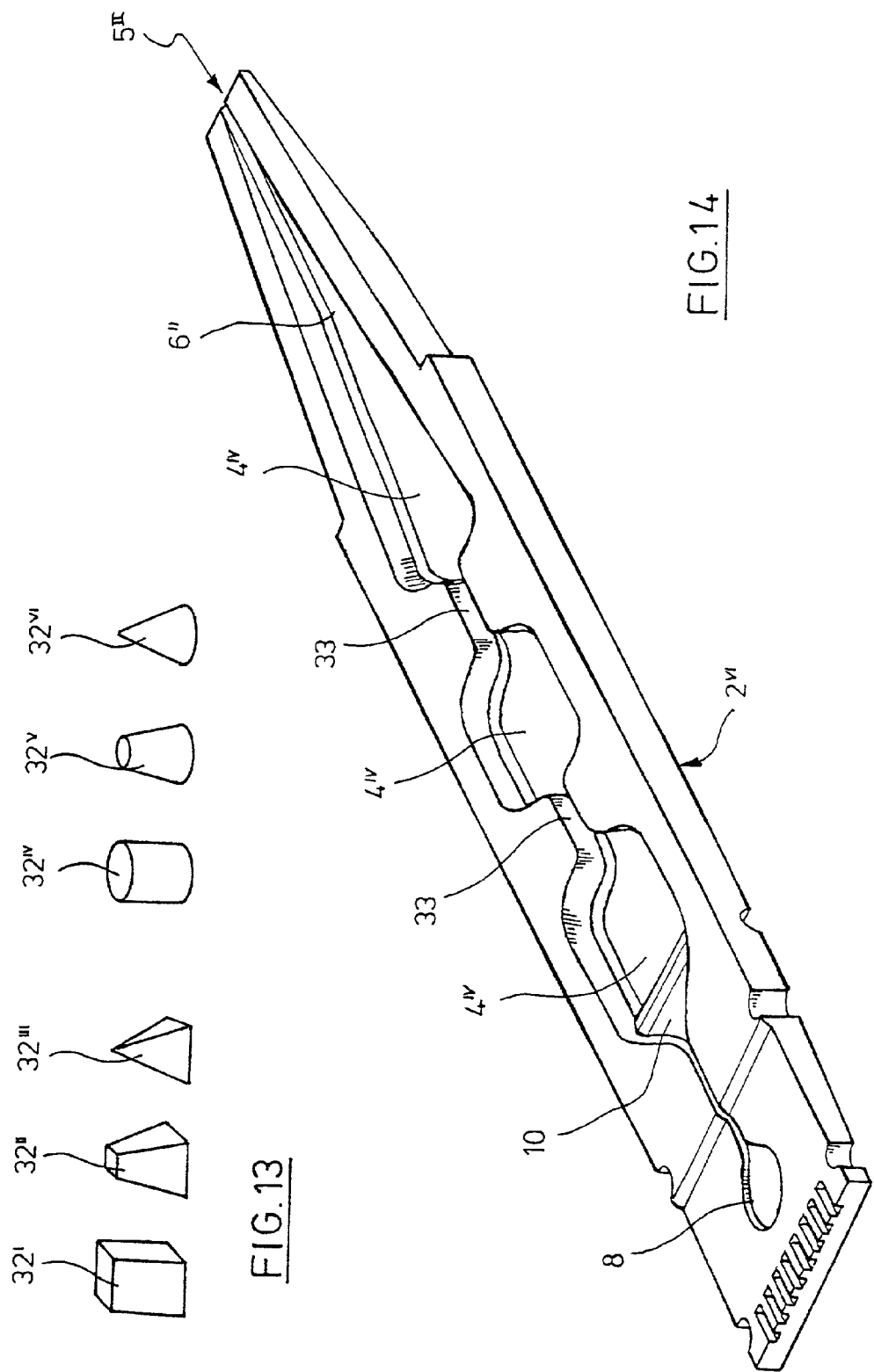

US 7,005,109 B2

SYSTEM FOR HANDLING LIQUID SAMPLES

RELATED APPLICATION

This application is a continuation of an International Application No. PCT/EP00/06213, filed Jul. 4, 2000 and designating the U.S.A.

BACKGROUND OF THE INVENTION

1. Field of the Invention

The invention relates to a device for handling liquid samples, a system for handling liquid samples, and a process for the manufacture of the device.

2. Description of the Prior Art

The handling of liquid samples or "sample handling" specifically comprises the proportioning (e.g. the pipetting, dispensing, loading of microtitration plates and gel electrophoretic plates), the transporting, centrifuging, tempering, and mixing of the samples, the closing (especially that of cells), cleaning, filtration, and concentration, the reaction of samples and/or reagents, and the measurement (especially the fluorimetric and photometric measurement) of samples.

The applicant has made known a system for handling liquid samples which comprises a multiplicity of various disposables (expendable articles which are discarded after a single or multiple use) and devices. This system is referred to as a "microtitration system" because the sample receptacles of the disposables have volumes in the range of some tenths to some thousandths of microliters. It comprises the following fields:

- Proportioning of volumes between 0.2 and 5,000 microliters using pipette tips or syringes along with appropriate proportioning devices,
- Sample transport, centrifuging, tempering, and mixing using reaction vessels for volumes of from 0.2 to 2.0 ml along with appropriate devices,
- Measuring equipment based on cuvettes and fluorimeters, luminometers, and photometers, and
- Cell manipulation (e.g. cell fusion, cell poration, and cell positioning) which is particularly based on cuvettes.

However, more and more smaller volumes and more and more higher spatial densifications of the volumes are used at an increasing tendency in all fields in the medical, biological or chemical laboratories. Since the end of the 80-ties, the microtitration plate which comprises a multiplicity of sample receptacles in the form of indentations lined up in rows next to each other has pushed its way instead of using individual reaction vessels, particularly in immunological analytics. As a result, the existing proportioning systems (e.g. the microliter pipette) were further improved to form multi-channel proportioning systems.

Initially, microtitration plates having 96 receptacles ("wells") were used in a 9 mm grid. Nowadays, it is particularly the methods for DNA multiplication (PCR) and for a DNA analysis which more and more frequently require working on a large number of samples in a highly parallel way. Thus, in the middle of the 90-ties, microtitration plates have become known which have 384 wells in a 4.5 mm grid measure. Microtitration plates having 1,536 wells in a 2.25 mm grid measure already exist meanwhile. These and further spatial densifications of the sample wells are expected to be more and more successful.

However, the development of the proportioning and vessel systems did not keep pace with the above described development. Multi-channel pipetting devices working with a multiplicity of pipette tips will meet the need to densify wells in microtitration plates only to a limited extent.

The manufacture of "gel loaders" also relies on pipette tips. For instance, pipette tips are stretched in an expensive second operation so as to form a thin gel loader tip or are flattened by pressure to have a thickness of 0.2 to 0.4 mm in order that they may be introduced into the narrow space between gel electrophoretic plates. These technologies do not allow high-degree parallelization and do not open up a possible way to reducing the dimensions with a view to reducing the grid measure for gels.

DE 198 43 691 A1 has made known a strip of tips comprising a number of interconnected pipette tips which are substantially disposed in parallel and are located side by side. The tips are hollow and each tip consists of a tip body and a flattened distal end. The flattened ends are substantially disposed in a plane in a coplanar manner, thus permitting the flattened ends to be introduced between tightly arranged plate surfaces of gel electrophoretic plates. Limits are also set to the spatial densification of this strip of tips which is intended to be manufactured from plastic, particularly by injection moulding.

The technology of integrating filtration elements into proportioning and vessel systems involves technical expenditure and is hardly suited for any further spatial densification. For instance, such filtration elements may serve as pipette tips to protect them from cross-contamination by aerosols or as filter inserts in reaction vessels or for bacteria cultures in membrane vessels or for microdialysis.

There is no integrated technical solution to enlarging the reaction surfaces for reaction vessels and pipette tips. As a rule, the insertion of cartridges and "columns" is resorted to which, via membranes or glass frits, communicate with the volume to be reacted.

Therefore, it is the object of the invention to provide a system for handling liquid samples and a process for the manufacture of the device for handling liquid samples, particularly for sample volumes of about 0.001 microliters and greater. It should be possible here to arrange such devices side by side at very short distances. Further, the devices should be adapted to be designed as disposables.

SUMMARY OF THE INVENTION

The object of the invention is achieved by a system for handling liquid samples, comprising at least one device for handling liquid samples having at least two superposed and interconnected planar elements between which a well for a liquid sample is formed which extends between an outwardly leading mouth to receive and/or deliver a liquid sample and an outwardly leading passage to connect the well to a displacement device for air or another gas.

The object of the invention is also achieved by providing at least one device for handling liquid samples having at least two superposed and interconnected planar elements between which a well for a liquid sample is formed which is connected to an outwardly leading mouth to receive and/or deliver liquid samples and has a displaceable limitation wall for displacing a fluid contained in the well which, for displacement, is adapted to be connected to an external actuation device.

The fact that the devices substantially comprise planar, superposed and interconnected elements makes it possible to realize wells particularly in the volume range of abt. 0.001 microliters and greater. Realizing volumes in the range of 0.001 to 20 microliters is of particular interest. The volumes of the inventive devices, however, may also be located in the range of conventional pipette tips and syringes (up to about 5,000 microliters) or vessels (up to about 2.0 ml). A plurality of devices may be arranged side by side at very short distances which correspond to the grid measure of newly developed microtitration plates. The spatial densification or parallelization is particularly favoured here by the fact that several devices may be formed side by side from common planar elements and/or several ones may be formed on top of each other from a plurality of superposed planar elements. The materials considered for the planar elements can be laminas, sheetings or membranes made of plastic and/or glass and/or semiconductor material and/or metal so that the devices can be manufactured at a relatively low cost and as disposables.

The devices allow themselves to be used for handling liquid samples in different ways. They may be resorted to, along with an appropriate apparatus, for proportioning liquids, i.e. receiving and/or delivering defined liquid volumes. This particularly includes the pipetting into, dispensing from, and loading of microtitration plates or gel electrophoretic plates in one channel or multiple channels each. In addition or instead, the devices may be used, alone or in conjunction with appropriate apparatuses, for transporting and/or centrifuging and/or tempering and/or mixing and/or as reaction vessels for liquid samples and/or reagents and/or for measuring liquid samples and/or reagents.

In any case, the sample liquid and/or reagents may be received and/or delivered by means of a displacement device or actuation device. Hence, the device for handling liquid samples can be filled with or emptied of liquid in a way similar to a pipette tip.

The system for handling liquid samples according to the invention comprises a handling apparatus having a displacement device, a device for releasably mounting the device for handling the liquid samples and a line sealingly connecting the displacement device to the passage if the device for handling liquid samples is disposed in the device for releasably mounting.

The other system for handling liquid samples according to the invention comprises a handling apparatus having an actuation device and a device associated therewith for releasably mounting the at least one device for handling liquid samples with the actuation device being coupled to the displaceable limitation wall of the device for handling liquid samples if the latter is disposed in the device for releasably mounting it.

The two systems make it possible to receive liquid samples in the device for handling liquid samples and/or to deliver them therefrom. This can be a proportioning operation or a procedure which takes place upstream and/or downstream of at least a further one of the aforementioned handling procedures (e.g. mixing, tempering). In an advantageous aspect of the handling apparatus, the system specifically allows the simultaneous parallel reception and/or delivery of liquid samples in or from a multiplicity of juxtaposed and/or superposed devices, e.g. with respect to the processing of microtitration plates.

According to another aspect of the present invention, the system for handling liquid samples comprises a handling apparatus with a centrifuge rotor which has at least one device for releasably mounting at least one device for handling liquid samples.

This system makes it possible to directly centrifuge a sample liquid which, for instance, has been filled into a device for handling liquid samples by means of a system described above, without any refilling operation. Also, the device for handling is particularly suited to be oriented, with its well, into the radial direction of the centrifugal machine in order to create favourable centrifuging conditions.

The system for handling liquid samples can include a handling apparatus with a heating device and at least one of these supports associated therewith for storing a liquid sample in at least one handling device supported thereon.

This system makes it possible to temper a sample received in a handling device with no refilling operation wherein particularly favourable conditions can be created for a heat exchange.

The system for handling liquid samples can also include a handling apparatus with an optical measuring device and a device for releasably mounting the device for handling liquid samples with the device for handling liquid samples, if disposed in the device for releasably mounting, is disposed with its well in the path of beams of the optical measuring device.

This system makes it possible for a liquid sample filled into a handling device to be readily subjected to an optical measurement. The measuring instrument concerned may be a fluorimeter, a photometer, a luminometer or another device for carrying out an optical, physico-chemical measuring method. Suitable aspects of the handling device may provide particularly favourable conditions for the optical measurement.

The elements of one or more handling apparatuses are disposed in or on at least one chassis and/or casing. In particular, a plurality of elements of various handling apparatuses may have a common chassis and/or casing. Even all of the elements of various handling apparatuses may be associated with a common chassis and/or casing.

Further, the at least one handling apparatus can be operable in a completely manual way and/or may work in a completely automatic way. The apparatus concerned, however, may also be an apparatus that works only in a partially automatic way. In addition, it is possible to design the at least one handling apparatus as a hand-held apparatus so that it can be held by the hand of a user for application.

Several handling apparatuses may interact automatically. To transport the device for handling, but also to support the handling apparatuses, an extra handling apparatus may be provided which may have a robot arm, for instance.

Finally, the object of the present invention is also achieved by a process for the manufacture of a device for handling liquid samples of an inventive system, wherein the surfaces of the planar elements are structured, a plurality of planar elements are brought into a relationship covering each other and are connected to each other and wherein the interconnected planar elements are broken up into individual devices for handling liquid samples in a direction perpendicular to the main plane of extension of the planar elements.

This manufacturing process allows to simply and precisely produce minimum-sized devices for handling liquid samples. This involves the possibility to manufacture them at a very low cost and to economically use the devices as disposables. By the way, what can be additionally achieved are measures to structure the liquid well and its surfaces which were not possible in previous devices for handling liquid samples, and to treat them chemically and modify them.

Some advantages of the invention are:

Because of their planar set-up, the devices for handling liquid samples can be parallelized at a high level in a two-dimensional way. The distance between the devices can be chosen to be extremely small. A multiplicity of devices may be juxtaposed in parallel with each other. This is an advantage, particularly for proportioning into high-density microtitration plates.

The devices for handling, because of their planar set-up (which comprises structured plastic/glass/laminas or plastic/ membrane/sheetings, for instance) need a very low height. This is a particular advantage for gel loaders. Sheetings and/or membranes of a small thickness may also be used if the devices for handling require flexibility. Small structural lengths can be achieved, particularly if the wells are given a special design (e.g. a meander shape).

Also, if gel loaders are manufactured from planar elements or sheetings a high-level parallelization will be possible for the first time and, at the same time, further possible options are provided to reduce the dimensions. This paves the way to reducing the reference grid measure for gel electrophoresis.

The mouth area (particularly the nozzle shape and pointed shape) may virtually be formed at will, particularly with respect to open-jet proportioning and introduction into narrow vessels.

The packing density of the handling devices can be largely increased as compared to the known microliter system. This is advantageous, in particular, in centrifuging machines and in disposing the devices for handling in multidimensional arrays.

The fact that the handling devices are thin-walled ensures a very rapid heat transfer. This is advantageous for special applications, e.g. in the PCR (polymerase chain reaction). If the handling devices are employed there it is possible to achieve very rapid tempering cycles.

The fact that the wells are closed from the environment prevents any cross-contamination. This specifically applies to designs having filtration membranes and to the version having a displaceable limitation wall.

Because of their low expansion, the devices for handling are particularly suited to be manufactured with modified surfaces, particularly those of plastic, with surface modifications (even coatings) being adapted to be made as an advantage because of the planar geometry.

It is very easy to provide the handling devices with filtration elements (particularly filtration membranes) which can be easily mounted on the planar geometries, e.g. by lamination.

Because of their small dimensions, the devices for handling also allow a further step towards an integration and miniaturization in the handling apparatuses.

The devices for handling in proportioning or a reaction allow to integrate technical solutions to increase the reaction surfaces by structuring the wells in an appropriate way.

The miniaturization of the devices and systems for handling involves a great advantage in fabricating (providing) them because of the reduced space they require.

The planar set-up of the handling devices is particularly advantageous in making automatic the provision of the devices for handling in a suitable dispensing system.

BRIEF DESCRIPTION OF THE DRAWINGS

More details and advantages of the invention ensue from the following (non-conclusive) description of possible embodiments which, in part, refer to the accompanying drawings. In the drawings:

FIG. 2 shows the connection and fixation areas of a proportioning disposable with a membrane filter in an exploded perspective view;

FIGS. 3a and b show a mouth portion of volume-receiving parts of the proportioning disposable of FIG. 1 (FIG. 3a) and a proportioning disposable having a nozzle-like taper (FIG. 3b) in a perspective side view;

FIG. 4 shows a proportioning disposable with a plurality of parallel juxtaposed proportioning disposables of FIG. 1 in an exploded perspective view;

FIG. 5 shows a planar element of another proportioning disposable in a perspective side view;

FIG. 8 shows a plurality of superposed proportioning disposables of FIG. 6 in a roughly schematic perspective side view;

FIG. 9 shows a proportioning disposable connected to a line leading to a displacement device;

FIG. 13 shows structural elements for a disposable in a perspective side view;

FIG. 14 shows the volume-receiving part of a reaction disposable in a perspective side view;

DETAILED DESCRIPTION OF THE PREFERRED EMBODIMENT

Figure 1:
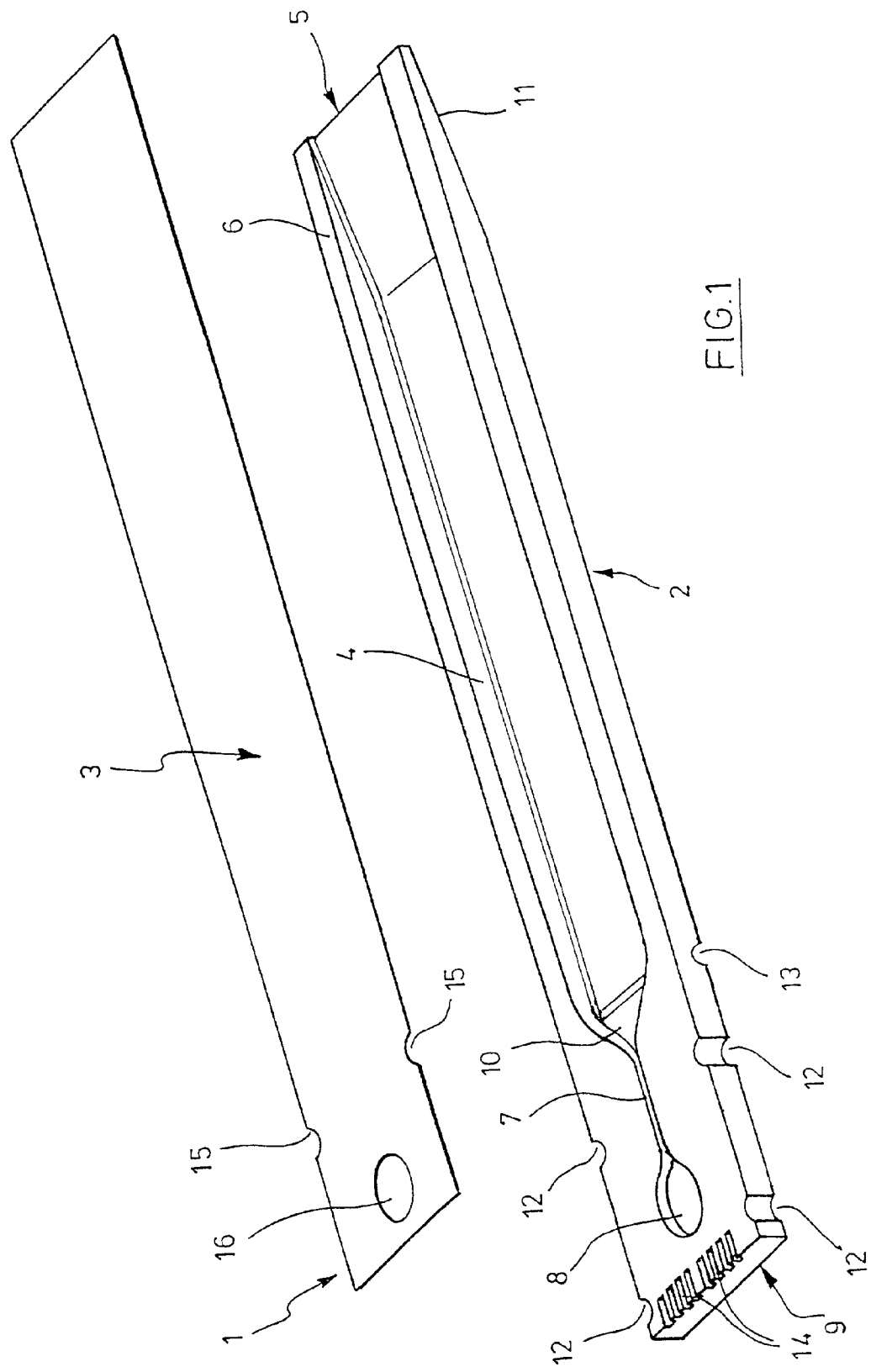
FIG. 1 shows a proportioning disposable in an exploded perspective view.

In the explanations of possible embodiments, the devices for handling liquid samples are referred to as "disposables" because these can be advantageously designed as expendable articles. Regardless of this, it is possible to design re-usable articles which are given the same features so that the explanations which follow apply to them as well.

1. Possible Fundamental Embodiments of the Invention

These may be disposables for receiving and/or delivering (particularly for proportioning) liquids. They may further comprise handling apparatuses for disposables, particularly for receiving and delivering (particularly for proportioning) liquid volumes.

The disposables concerned may further be disposables for other types of sample handling. Sample handling may include transportation, centrifuging, tempering, and mixing. Moreover, the disposable may serve as a reaction vessel for liquid samples and/or reagents. All handlings can be performed in a single disposable. This may include manual or automated handling apparatuses, particularly for centrifuging, tempering (specifically for the PCR) or mixing.

In addition, disposables are possible for measuring liquid samples and/or reagents, and handling apparatuses belonging thereto for optical measurement.

In addition, disposables are possible which have integrated filtration elements of any type, e.g. hydrophobic aerosol barriers (similar to the currently used filters made of sintered PE or PP), hydrophobic filters for aeration and deaeration (for vessels to breed bacteria in) or membranes for microdialysis.

Further, disposables are possible which have integrated structures to geometrically enlarge reactive surfaces.

All of the disposables comprise two or more planar elements. These may include, in particular, lamina of plastic, glass or silicon, sheetings or membranes.

The function of these planar elements corresponds to the aim set for the disposable concerned, e.g. by the inner structure given to the individual planar elements (e.g. having fluid channels, mixer structures, surface enlargements).

Surface modification is further considered in defined functional fields (e.g. to functionalize surfaces in an active/reactive or passive way; amino groups, carboxyl groups, streptavidin, immobilized enzymes, oligos, hydrophilizing, hydrophobizing, electroplating).

In addition, connection to additional functional elements is possible. For instance, these may include membranes, nonwoven fabrics, optical windows, aeration filter, and electrodes.

The external geometry may be chosen so as to consider the application concerned (e.g. a small, flat tip for gel loaders).

2. Manufacturing Process

The fact that the structures are realized on planar elements makes it possible (similarly to the manufacture of components in the semiconductor industry and micro-system technology) to simultaneously process a large number of disposables on a plate (similarly to the wafers in the semiconductor industry or micro-system technology) or another planar element.

The manufacture of the disposables may be performed in several steps:

Initially, the surfaces of the planar elements may be structured.

Afterwards, one or more surface treatment steps may be and are taken, if required, with a view to functionally modifying the surfaces of the planar elements in defined areas.

Subsequently, two or more planar elements may be connected to each other (e.g. by laminating or bonding them).

Finally, the disposable may be separated from each other, if desired.

3. Technologies of Manufacture

Manufacture can be effected on the basis of known technologies. Many methods are suited for structuring the surfaces, e.g.

(Hot) embossing or injection moulding for planar plastic material (e.g. laminas or sheetings)

Laser-beam or water-jet cutting in sheetings made of plastic (particularly for small series)

Micromechanical machining (particularly for small series)

Etching techniques (wet or dry) for glass and silicon.

For instance, the modification of surfaces may be carried out by means of chemical surface treatments (e.g. polymer grafting, etching techniques, electroplating processes), by means of plasma processes (e.g. corona treatment) or plasma coating processes or by means of CVD (chemical vapour deposition) or PVD (physical vapour deposition).

The joining technologies to be employed depends on the combination of materials and may include, for instance, glueing (e.g. lamination using sheetings), ultrasound welding, friction welding, and joining by means of thermal processes (e.g. bonding processes).

For instance, the separation and/or shaping of the outer contour of disposables may be accomplished by cutting (e.g. diamond sawing as is known in the silicon technology, laser beam or water jet cutting processes) or by stamping processes.

4. Interface Between Disposable and Handling Apparatus

It is possible to perform two or more steps of sample handling by using one and the same disposable. This specifically includes proportioning, centrifuging, filtering, tempering, mixing, reacting, measuring, analyzing, cell manipulation (e.g. cell poration, cell fusion, cell positioning), etc.

Some details of disposables and handling apparatuses for carrying out various handling steps are explained below. These details may occur in a more or less cumulated way on one and the same disposable or handling apparatus.

a) Proportioning Disposables

The planar disposable may be adapted to be inserted into a handling apparatus. Here, the passage of the disposable may be brought into a sealing contact with the apparatus. A slidable sealing surface and/or an O-ring may exert its effect at this point. The contacting action may further be supported by a contact element which can be a spring, an insertion slope or the like.

After the sealed contact is made proportioning may be controlled by displacing an air column by means of a displacement device similar to the pipetting process of an air cushion pipette. The march of pressure desired may be produced via a piston-and-cylinder system (similar to that of a piston pipette) or by means of miniaturized pumps (which have been developed already now in the silicon and/or plastics technologies).

The options possible in microstructuring allow to keep very low the dead space in the disposable and the handling apparatus, i.e. the volume of the air column, in the interest of keeping the volume error as small as possible and achieving high precision in proportioning. This permits to effect pipetting and dispensing with one type of a disposable.

If disposables are used which have a displaceable limitation wall the contact with the handling apparatus has to ensure that the actuation device be connected to the limitation wall in order to displace it. This makes possible a direct effect of an actuation mechanism on the limitation wall. However, a hydraulic actuation, a magnetic actuation or the like are possible as well.

The surface of all disposables may be made hydrophilic or hydrophobic with a view to compensating annoying capillary forces.

b) Centrifuging and Filtration Disposables

Planar disposables for centrifuging may be arranged in a centrifuge in a way similar to that of small sample tubes in a hematocrit centrifuge. Sealing the vessel is possible, in particular, by means of a cover (e.g. a plate or sheeting) on the disposable or in the centrifuge itself It is also imaginable to equip the centrifuging disposables as proportioning and/or filtration disposables. Also, the location where to position pellets in such a disposable may be defined better than in a conventional reaction vessel.

c) Tempering/PC Disposables

The proportioning and tempering functions can be advantageously realized by a type of disposable, particularly with regard to the implementation of the PCR process and the concurrent cyclic temperature changes.

Contacting a heat-conducting surface (which preferably has a higher thermal capacity), which may assume various adjustable temperatures (even in a cyclic change) in the planar disposables, can favourably be effected via a cover sheet of a small thickness. This one is ideally suited for optimum heat transition if it has a thickness of from a few $\mu$m to some 100 $\mu$m. Moreover, a particularly heat-conductive material may be selected for the cover sheet whatever the material of the planar element is.

Besides, planar disposables make it possible to nearly randomly reduce the sample volume and reaction volume by reducing the depth of the well. This gives the sample volume a very low thermal capacity, which permits to achieve short heating and cooling times, which is very advantageous for the PCR in reducing the cycle time.

The volume of the well may be adjusted specifically by forming its depth in a planar element. This is particularly advantageous because the depth can be reduced to virtually any extent.

The integration of the sample well, the provision of the reagents (enzymes and primers), and the PCR process proper can be achieved in a single planar disposable. At the same time, this provides the possibility of integrating the reaction chemistry and to provide for a thin-walled reaction space (on either side, if needed) in an extent exceeding that for deep-drawn sheetings) in order to achieve more rapid temperature cycles.

d) Analytical Disposables

A planar disposable makes it feasible to integrate the sample well and the reaction and analysis (measurement and evaluation). Also, the multi-channel structure which is required nowadays can be realized in a simple manner.

The planar arrangement favours its use in the ATR (Attenuated Total Reflection) photometry and infrared spectroscopy. Also for ultraviolet spectroscopy, suitable cuvettes permeable to ultraviolet radiation may be created by means of the planar set-up and the known PFA sheetings having a thickness of less than 100 $\mu$m.

The thin-walled structure of a planar disposable is also advantageous for the detection of fluorescence and luminiscence signals. Plastics are known that have a low inherent fluorescence.

e) Disposables for Bacteria Cultures/Microdialysis

The planar disposables allow to integrate the sample well and to carry out a bacteria culture or microdialysis. The high surface/volume ratio makes possible a very efficient gas exchange for aeration and a very efficient dialysis.

For instance, planar disposables laminated by sterile membranes (those having a pore size of 0.25 m and 0.45 $\mu$m being commercial) or hydrophobic aeration membranes, for instance, may be used as vessels for bacteria cultures.

f) Cell Manipulation Disposables

The planar disposable allows to integrate the sample well and cell manipulation (e.g. cell poration, electric poration), cell fusion or cell positioning). More process steps can be integrated. The arrangement is such as to permit to easily integrate moving and poration electrodes in order to separate cells and cell porations from each other.

Electroplating methods or vapour deposition processes make it possible to provide the disposable (similarly to the way for an electric poration cuvette) with electrodes (e.g. in aluminum, gold). The distance between electrodes may be largely chosen at will here. The cells treated by electric poration can be dispensed again after the operation along with the disposable which can also be a proportioning disposable. There is no need for refilling them into the electric poration cuvette and filling them back via pipette tips.

Spiral-shaped electrode structures which are employed for cell fusion may be substituted for by planar meander-shaped or comb-shaped electrode structures on the planar disposable.

5. Description of the Figures

Details of the aforementioned and further embodiments which are possible will now be explained with reference to the drawings. The appertaining description is valid for all embodiments concerned to the extent to which identical reference numbers have been used for features of different embodiments. This also applies to identical reference numbers which are provided with one index or more indices with the different numbers of indices marking differences which are explained in greater detail in the description of the figures.

FIG. 1 shows a version of an embodiment of a single proportioning disposable 1 which consists of two superposed planar elements 2, 3 having an elongate shape or tongue-like shape.

The planar element 2 can also be referred to as a "volume-receiving part" because it has formed therein the well 4 for a liquid sample, which has the shape of a wide channel extending in the longitudinal direction of the planar element 2. The well 4 has a mouth 5 at a narrow end side of the planar element 2. The depth of the channel-shaped well 4 gradually decreases in a nozzle portion 6 towards the mouth 5. The nozzle portion 6 extends over approximately one quarter of the overall length of the wide portion of the well 4.

At the other end, the well 4 is connected to a small cup-shaped secondary well 8 via a channel 7 of a significantly smaller cross-section. This one is disposed in the vicinity of the end side 9 which is located opposite the end side where the mouth 5 is.

The well 4, via a tapering and rising transition area 10, passes over into the channel 7 which is narrower and is of a depth which is noticeably smaller. The secondary well 8 is of the same reduced depth as is the channel 7.

All edges of the sample well 4 and those of the channel 7 and the secondary well 8 are rounded to minimize the adherence of liquid ("residual moisture"). Hydrophilic plastics or materials of the planar elements can be made hydrophobic to reduce such adherence or, vice versa, hydrophobic plastics can be made hydrophilic.

In the narrow longitudinal sides, in the vicinity of the end side 9, the planar element has two semi-cylindrical recesses 12 each that serve as positioning elements, i.e. aids for precisely aligning the planar element 2 in a handling apparatus.

In the lower, wide longitudinal side, the planar element 2 has another semi-cylindrical recess 13 which serves for being locked with a handling apparatus.

Directly adjacent to the end side 9, on its upper, wide longitudinal side, the planar element 2 has a code 14 in the form of a certain array of indentations, elevations, holes, magnetized points, electrically conducting areas or the like which can be sensed by the sensing device of a handling apparatus to determine the type of the disposable.

The volume-receiving part 2 can preferably be manufactured as an embossed or injection moulded component, particularly from a transparent plastic. Its thickness typically is from 0.2 to 1.0 mm. Because of its planar structure, this component also is excellently usable for being coated (e.g.

with reactive groups—COOH, —$N_4$, for hydrophobizing or hydrophilizing). The depth of the channels typically is less than 0.1 mm.

The planar element 3 is a thin covering sheeting which can also be transparent. The thickness of the sheeting can typically be from 50 to 200 µm.

The cover sheeting 3 can be connected to the planar element 2 by means of the aforementioned joining technologies. It will then close the well 4 and the channel 7. In the peripheral area, the cover sheet 3 has semicircular recesses 15 which come to coincide with two recesses 12 of the planar element 2.

The code 14 is not covered by the cover sheeting 3 in order to allow the interrogation contact with a sensing device. The cover sheeting 3 further has a passage 16 which is disposed exactly above the secondary well 8.

Thus, a displacement device of a handling apparatus can be connected to the proportioning disposable 1 through the passage 16. A negative pressure or positive pressure applied to the passage 16 serves for drawing a sample liquid into the well 4 and for expelling it therefrom.

The planar elements 2, 3, particularly the cover sheeting 3, are preferably chosen to be of a very rigid material in order to prevent undesirable effects in proportioning.

In conjunction with dispensing disposables, however, it is also possible to use a very elastic sheeting (with no passage 16) in which proportioning is effected by simply compressing the enclosed volume, e.g. by means of an appropriately shaped ram, i.e. via a direct displacement ("positive displacement") (not shown in FIG. 1).

The approximate dimensions of the disposable which is shown are: 2.25 mm in width, 0.5 mm in height, 15 mm in length. The volume of the well 4 is about 5 microliters.

FIG. 2 shows a region of another proportioning disposable 1' the single difference of which from the proportioning disposable 1 of FIG. 1 is that it has an additional planar element 17 in the form of a membrane sheeting which is disposed between the passage 16 and the secondary well 8. The membrane sheeting 17 can be a membrane as is used for sterile filtration where the pore sizes are 0.2 µm or 0.45 µm, for instance. The membrane sheeting 17 serves for filtering the suction air to avoid the contamination of the handling apparatus to be joined to the passage 16. The membrane sheeting 17 is intended to cover the passage area of the suction air so that it is sufficient for it to slightly project beyond the edge of the passage 16 or that of the secondary well 8. In the example, it is approximately of a square shape with its width corresponding to the width of the covering sheeting 3.

The thickness of the membrane sheetings 17 can typically be from 0.01 to 0.1 mm. The planar element 2 may have an indentation (not shown in FIG. 2) for membrane sheetings of larger thickness or non-woven filtration fabric.

FIGS. 3a and b show versions of the mouth area of proportioning disposables. Only the volume-receiving parts 2, 2' are shown with no cover sheetings.

According to FIG. 3a, the planar element 2 has a well 4 the depth of which decreases to 0.1 mm at the mouth in the nozzle region 6. In this aspect of the mouth 5, it is possible to deliver a jet which is relatively wide.

According to FIG. 3a, however, it is not only the depth which decreases, but also the width of the well 4' towards the mouth 5' in the nozzle region 6, namely at an angle of 7 to 8°, as a maximum (see the diffusor theory). As a result, a heavily accelerated jet is reached which is of a small width. In addition, the planar element 2' has a chamfer 11 not only at the lower, wide longitudinal side, but has further chamfers 11' at the narrow longitudinal sides so that it is pointed altogether towards the mouth 5'. This can be useful, e.g. for gel loaders or the reception in or delivery from microtitration plates (primarily those in a parallel arrangement).

The pointed shape of the proportioning disposable may be obtained by means of known manufacturing technologies such as cutting or punching.

FIG. 4 shows a proportioning disposable 1" which is formed from a multiplicity of juxtaposed proportioning disposables 1' as are shown in FIG. 2. Here, the proportioning disposables 1' are integrally interconnected to form the proportioning disposable 1".

For this purpose, the proportioning disposable 1" has a single volume-receiving part 2" which is composed of a plurality of parallel juxtaposed volume-receiving parts 2.

The proportioning disposable 1" further has a single strip-shaped membrane sheeting 3' which extends across all of the secondary wells 8 of the volume-receiving part 2".

The proportioning disposable 1" further has a single covering sheeting 17' which is composed of a plurality of parallel juxtaposed covering sheetings 3 and has all of the passages 16 which are associated with the secondary wells 8 in the volume-receiving part 2".

The elements 2", 17', and 3' are superposed and connected to each other in such a way that this results in a proportioning disposable 1" which has a multiplicity of parallel juxtaposed proportioning disposables 1' which are integrally connected to each other.

A parallel arrangement of eight proportioning disposables 1' is shown. It is adapted to process usual 96-well microtitration plates, for instance. However, if the set-up is appropriate densities may be achieved which are even higher in order to process 384-well or 1536-well microtitration plates or others having any grid dimensions. To this end, advantageously pointed shapes may be introduced reference to which will be made below by means of another drawing.

The proportioning disposable 1" interacts with a handling apparatus the one or more displacement units are sealingly connected to all of the passages 16.

Generally, the grid dimension of the mouth 5 can be adapted to any grid measure for proportioning (e.g. to receive microtitration plates) on a portion of the proportioning disposable 1" irrespective of an adaptation to a reception measure of a handling apparatus for the passages 16. This permits working on different microtitration plate grid measures by means of a handling apparatus and appropriately modified disposables 1".

The particular features of the volume-receiving part 2''' shown in FIG. 5 for a proportioning disposable, on one hand, are that it has an indentation in the form of a shoulder 18 which serves for depositing a thicker membrane sheeting 17. Such an indentation was referred to already when FIG. 2 was described.

Another particular feature of this volume-receiving part 2''' is that it has a well 4" with a nozzle portion 6" which tapers towards the mouth 5" more than it does in the embodiment of FIG. 3b.

Finally, the volume-receiving part 2''' has its narrow longitudinal sides provided with steps 19 which face the end side having the mouth 5". The narrow longitudinal sides 11" extending from the steps 19 to the end side having the mouth 5" enclose an angle which is more acute than that of the embodiment of FIG. 3b.

This volume-receiving part 2''' is fitted with a membrane sheeting which exactly fits onto the shoulder 18 without covering the code 14 and the recesses 12. The upper surface of the membrane sheeting and that of the adjacent portion of the volume-receiving part $2'''$ are at the same level. Then, the membrane sheeting and the portion of the volume-receiving part $2'''$ which is adjacent at the same level are covered with a covering sheeting the outer contour of which exactly corresponds to that of the regions to be covered.

Because of the heavily pointed areas near the mouth $5''$, the completed proportioning disposable is particularly suited for insertion into narrow vessel apertures. It may then be supported at the vessel edge by means of the steps 19.

The example of FIG. 5 corresponds to that of FIG. 1 in its width, length, and height. The volume of the well $4''$ is about 4.6 microliters, which corresponds to a depth of the well $4''$ of 0.5 mm and a maximum width of 1.3 mm.

Figure 6:
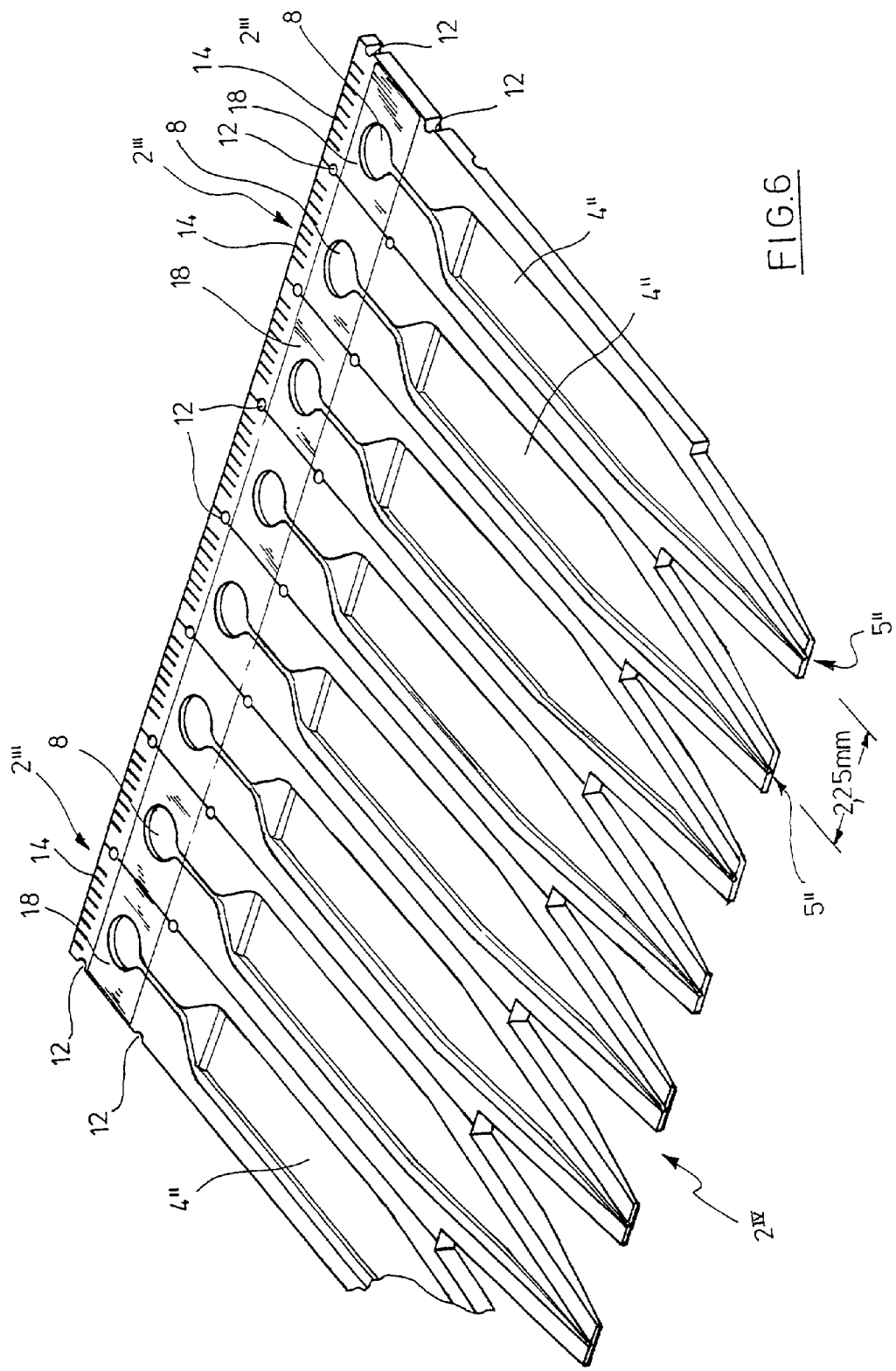
FIG. 6 shows a volume-receiving part of a proportioning disposable with a plurality of parallel juxtaposed volume-receiving parts of FIG. 5 in a perspective side view.

FIG. 6 shows a volume-receiving part $2^{IV}$ which is composed of parallel juxtaposed volume-receiving parts $2'''$ which are integrally connected to each other. In accordance with the width of each volume-receiving part $2'''$ which is 2.25 mm the distance between adjoining mouths $5''$ or channels is 2.25 mm. This adjusts the volume-receiving part to the grid distance of the marketable microtitration plates having 1,536 wells (32×48 wells). However, the number and distance of the individual channels can be generally chosen at will.

A proportioning disposable is manufactured by means of the volume-receiving part $2^{IV}$ by placing thereon a membrane sheeting strip which covers all of the shoulders 18, but leaves open the codes 14 and the recesses 12. The upper surface of the membrane sheeting strip and the portion of the volume-receiving part $2^{IV}$ which joins at the same level will be coated by a cover sheeting the outer contour of which corresponds to the outer contours of the aforementioned regions.

Figure 7:
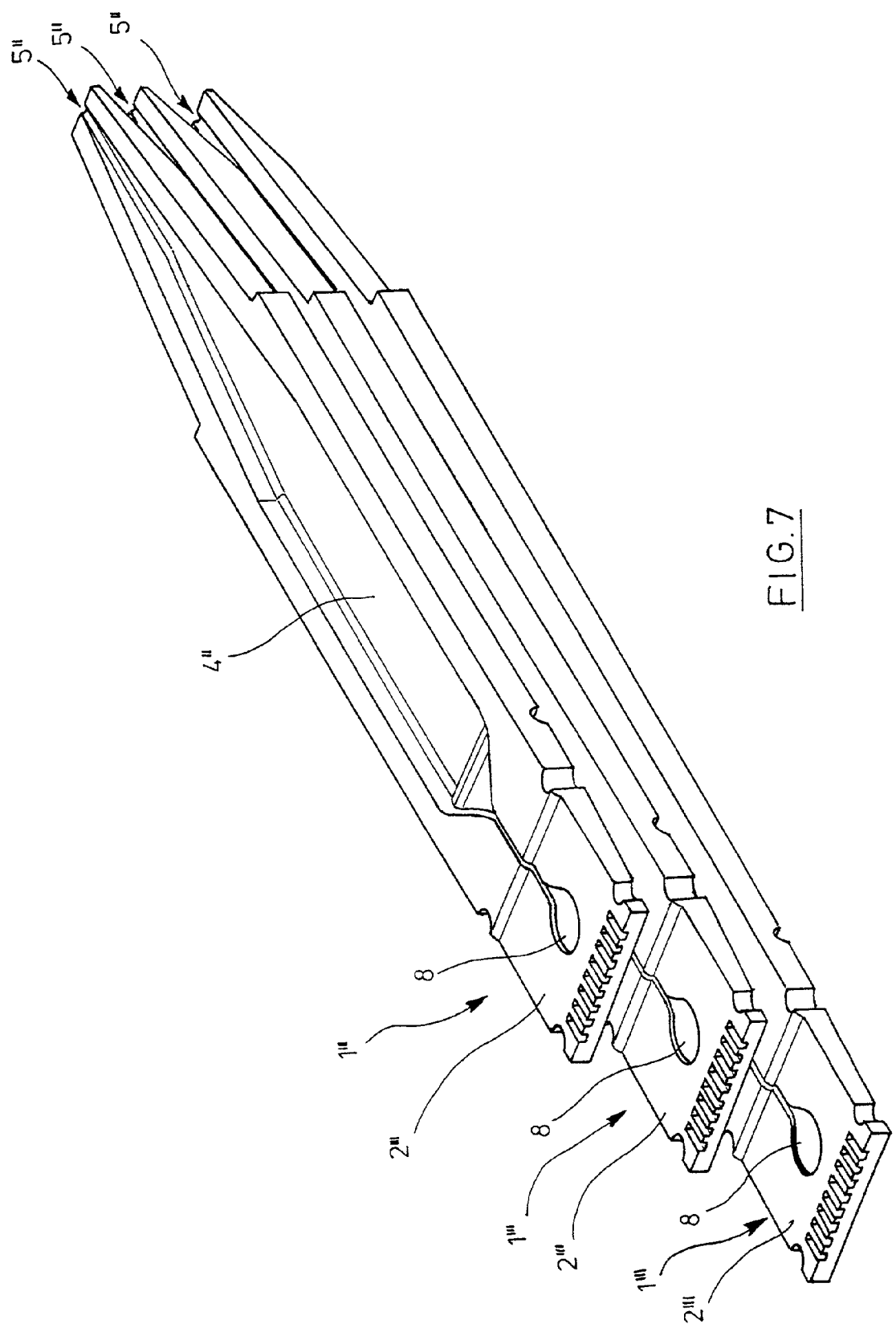
FIG. 7 shows a plurality of superposed proportioning disposables of FIG. 5 in a perspective side view.

FIG. 7 shows a parallelization by arranging several disposables $1'''$ on top of each other (by a pile-up).

What is shown are the volume members $2'''$. It is understood, however, that all of the volume members $2'''$ will be completed by membrane sheetings and cover sheetings in the above-described way.

The proportioning disposables are of different lengths in order to connect all of the secondary wells 8 (or passages of the cover sheetings placed on top) to a displacement device.

The different length of the proportioning disposables is possible without any problem because the "dead space" is minimized in the area of the channels 7. It is understood here that the wells $4''$ for liquid are of the same size in all volume-receiving parts $2'''$, but the channels 7 are of different lengths to connect the secondary wells 8 arranged at different positions to the wells $4''$.

The minimization of the dead space by the channels 7 of the various proportioning disposables $1'''$ should coincide with a minimization of the dead space, if possible, also in the hand-held apparatus for the proportioning of liquids. Details on the dead space problems and the volume errors related thereto can be deduced, for instance, from EP 0 562 358 B1 "Method for correcting the volume error in designing a pipetting system".

If the height of the proportioning disposable is 0.5 mm as is indicated in an exemplary way for FIG. 5 the distance between the mouths $5''$ of adjacent proportioning disposables, accordingly, also is only 0.5 mm in the arrangement of FIG. 7.

FIG. 8 shows how to superpose proportioning disposables $1^{IV}$ on the basis of the volume-receiving part $2^{IV}$, which is shown in FIG. 6, in a roughly schematic way. Again, the proportioning disposables $1^{IV}$ are of different lengths in order to allow an access to the secondary wells 8. However, they are disposed in a common plane at the mouths $5''$.

FIG. 9 illustrates how to connect a proportioning disposable 1 having a line 20 to a displacement device 21 which is drawn at a reduced scale. The line 20 sealingly rests on the upper surface of the of the covering sheeting 3 via an O-ring 22 with the O-ring 22 surrounding the passage 16. This connects the line 20 to the well 4 of the disposable 1 via the secondary well 8 and the channel 7.

The sealing contact of the disposable 1 bearing on the O-ring 22 is intensified by a spring mechanism 23 which acts in the direction of the arrow F. Next to the end side 9 at bottom, the proportioning disposable 1 may have a chamfer which supports the bear-on operation.

The displacement device 21 is formed by a cylinder 24 with a piston 25 which is slidable therein and is adapted to be actuated by means of an actuation button 26. Thus, displacing the piston 25 in the cylinder 24 can draw liquid into the disposable 1 through the mouth 5 or can expel it from the mouth 5.

The other disposables mentioned as examples may also be filled and emptied in this manner.

Figure 10:
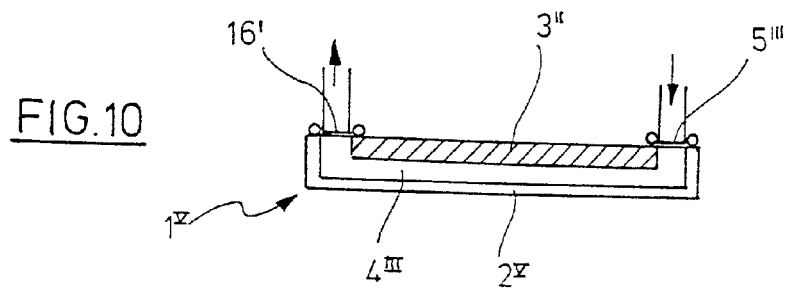
FIG. 10 shows a centrifuging disposable in a roughly schematic longitudinal view.

Referring to FIG. 10, a centrifuging disposable $1^V$ has a volume-receiving part $2^V$ with a well $4'''$ in the form of an elongate channel. On the side in which the well $4'''$ is inserted, the volume-receiving part $2^V$ is covered by a cover plate or cover sheeting $3''$ which has a first aperture or mouth $5'''$ for being filled and emptied and a second aperture or passage $16'$ for being connected to a displacement device (with the apertures also being usable in the opposite way).

The apertures $5'''$ and $16'$ are sealed during the centrifuging operation, e.g. by closing lids (not shown) which can be hinged to a cover plate $3''$ via film hinges. Also, separate cover elements may be provided, reference to which will be made below.

Figure 11:
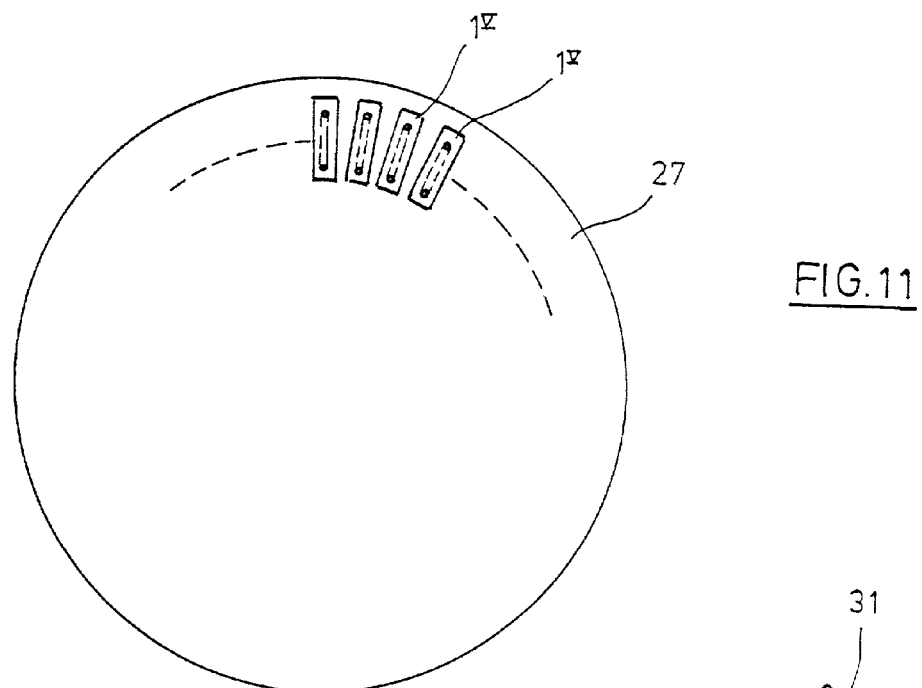
FIG. 11 shows several centrifuging disposables according to FIG. 9 in a centrifuge rotor.

Referring to FIG. 11, a plurality of centrifuging disposables $1^V$ according to FIG. 10 are arranged on a centrifuge rotor 27 in a radial alignment. The centrifuge rotor 27 may have wells in which the centrifuging disposables $1^V$ are held in order to take account of a uniform mass distribution by an appropriate arrangement of the centrifuging disposables $1^V$ or balancing weights. The mass balance problem is diminished by the small mass of the centrifuging disposables $1^V$.

Figure 12:
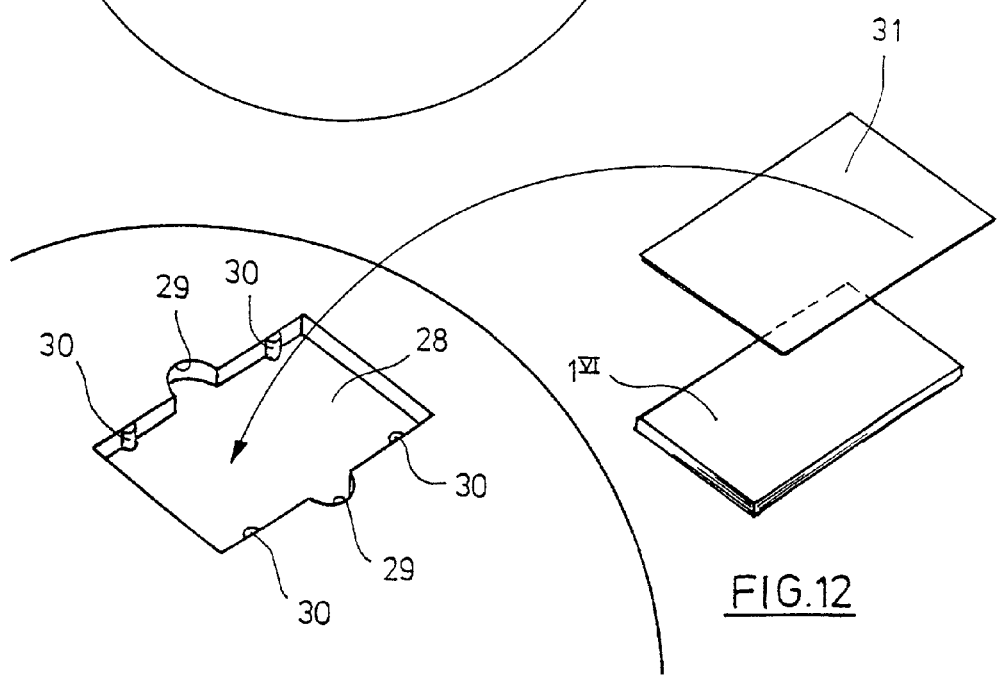
FIG. 12 shows a centrifuge rotor having a well for a centrifuging disposable in a perspective side view.

Referring to FIG. 12, a centrifuge rotor 27 has wells 28 which essentially are complementarily formed into centrifuging disposables $1^{VI}$. A disposable $1^{VI}$, to be centrifuged may be formed in its longitudinal section in the way shown in FIG. 10. It can be a disposable which has one or more parallel juxtaposed wells $4'''$ (e.g. a disposable having 8, 16, 32 well lines).

At two opposed edges, the wells 28 have recessed grips 29 which make it easier to remove the proportioning disposables $1^{IV}$ from the well 28.

Further, the wells 28 have arranged therein centering elements 30 in the form of projections at the insides of the edges, which provide for a tight-fitting seating of the planar disposable $1^{VI}$ in the well 28.

A cover 31 is intended to sealingly close the apertures (not shown) at the upper surface of the disposable $1^{VI}$. The part concerned may be a plastic part which (with respect to the apertures of the disposable $1^{VI}$) is fully or partially provided with an elastic layer which ensures a liquid-tight closure.

The cover 31 is also held by the centering elements 30 in the well 28 in a tight-fitting relationship. The centering elements 30 may have a certain elasticity to clamp the disposable $1^{VI}$ and the cover 31 in place.

The cover 31 provides that no liquid exits from the disposable $1^{VI}$ under the action of centrifugal forces.

FIG. 13 shows various structural elements which can be formed in order to increase the surface and/or stimulate turbulence and/or produce a shear force on a wall of a well of a disposable. Preferably, several elements of one of the types shown or several types are produced at the bottom of the well of one of the previously explained volume-receiving parts.

In FIG. 13, the structural elements $32'$ to $32^{VI}$ may have the shape of a box ($32'$), a truncated pyramid ($32''$), a pyramid ($32'''$), a cylinder ($32^{IV}$), a truncated cone ($32^{V}$) or a cone ($32^{VI}$). The advantage of the elements $32''$, $32'''$, $32^{V}$, $32^{VI}$ is that they have slopes for release from a mould.

A disposable the well of which is provided with such structural elements $32'$ to $32^{VI}$ may be used to thoroughly mix a sample liquid by introducing one or more pressure surges into the sample liquid by means of a displacement device (or an actuation device).

Such structural elements are also advantageous with regard to the performance of reactions in the disposable. As a principle, the function of liquid reception in planar disposables may be ideally combined with various requirements of a reaction vessel. Other structural measures can be considered with regard to specific reactions.

Thus, in a volume-receiving part $2^{VI}$ of FIG. 14 (as opposed to the volume-receiving part $2'''$), the wells may be distributed to various well portions $4^{IV}$ which are connected to each other via connection channels 33 the cross-section of which clearly falls below the one of the well portions $V^{IV}$.

The first well $4^{IV}$ also has the nozzle portion 6" and the mouth 5".

The last well $4^{IV}$ is connected to the channel 7 and the secondary well 8 via the transition portion 10.

The middle well portion $4^{IV}$ is connected to the first and second well portions $4^{IV}$ via the connection channels 33.

It is specifically for this disposable, which is also completed by a membrane sheeting and a cover sheeting, that the connection channels 33 can be made hydophilic.

All of the disposables provide the possibility to coat the well. It is also possible here to realize (complex) different functions (e.g. functional groups, enzymes, hydrophilic or hydrophobic properties) in one disposable by partially covering it while the well is being coated or one or more well portions are being coated. Reagents or co-reactants (particularly enzymes) for complex reactions may also be made available in an immobilized, wall-linked shape.

Figure 15:
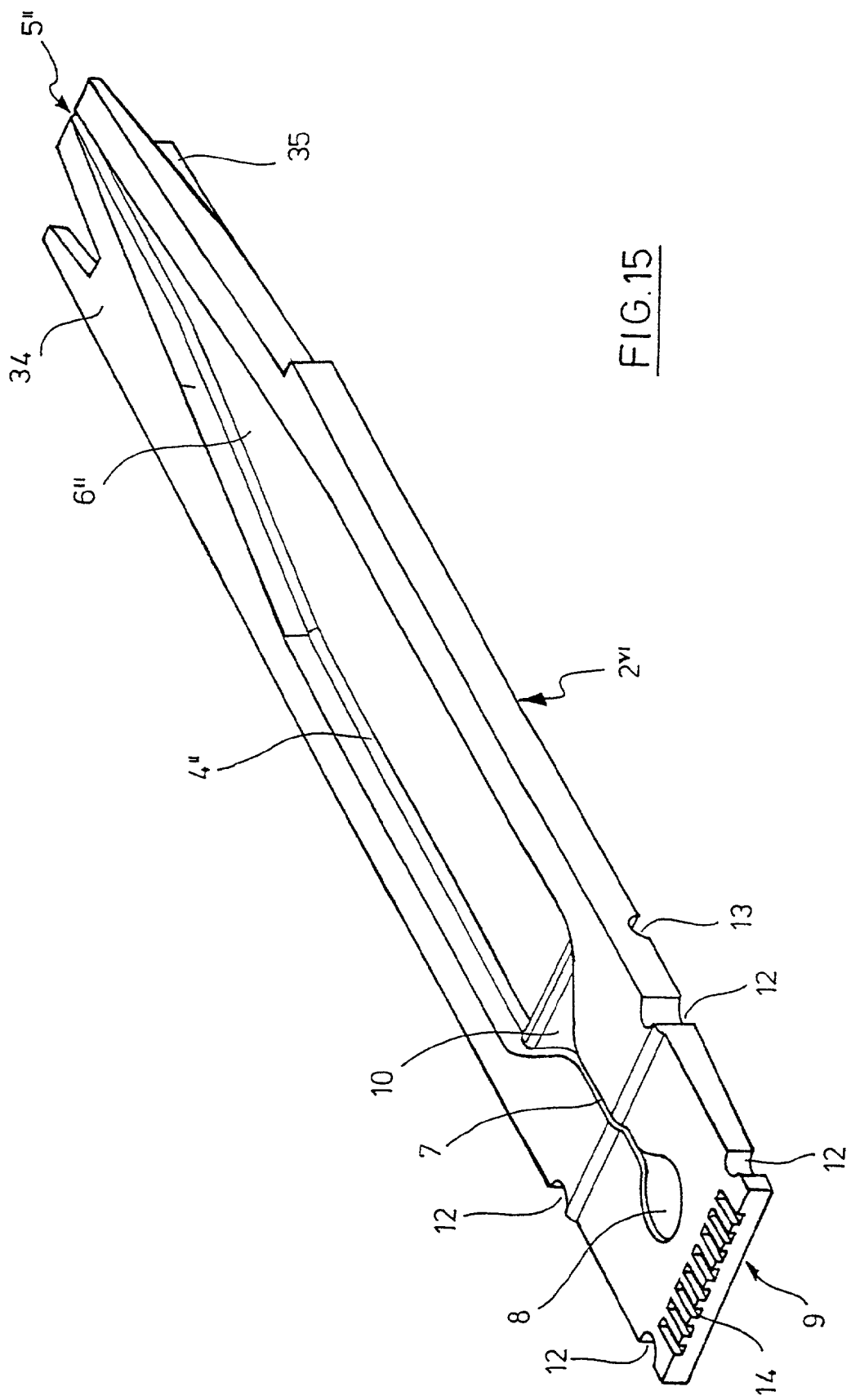
FIG. 15 shows the volume-receiving part of a gel disposable in a perspective plan view.

The volume-receiving part $2^{VII}$ for a proportioning disposable of FIG. 15 is distinguished from the volume-receiving part $2'''$ of FIG. 5 by the fact that it has a threading aid 34 on one side or two sides to facilitate the supply of electrophoretic gel plates. In addition, a step 35 exists to act as a support in supplying electrophoretical gels.

Figure 16:
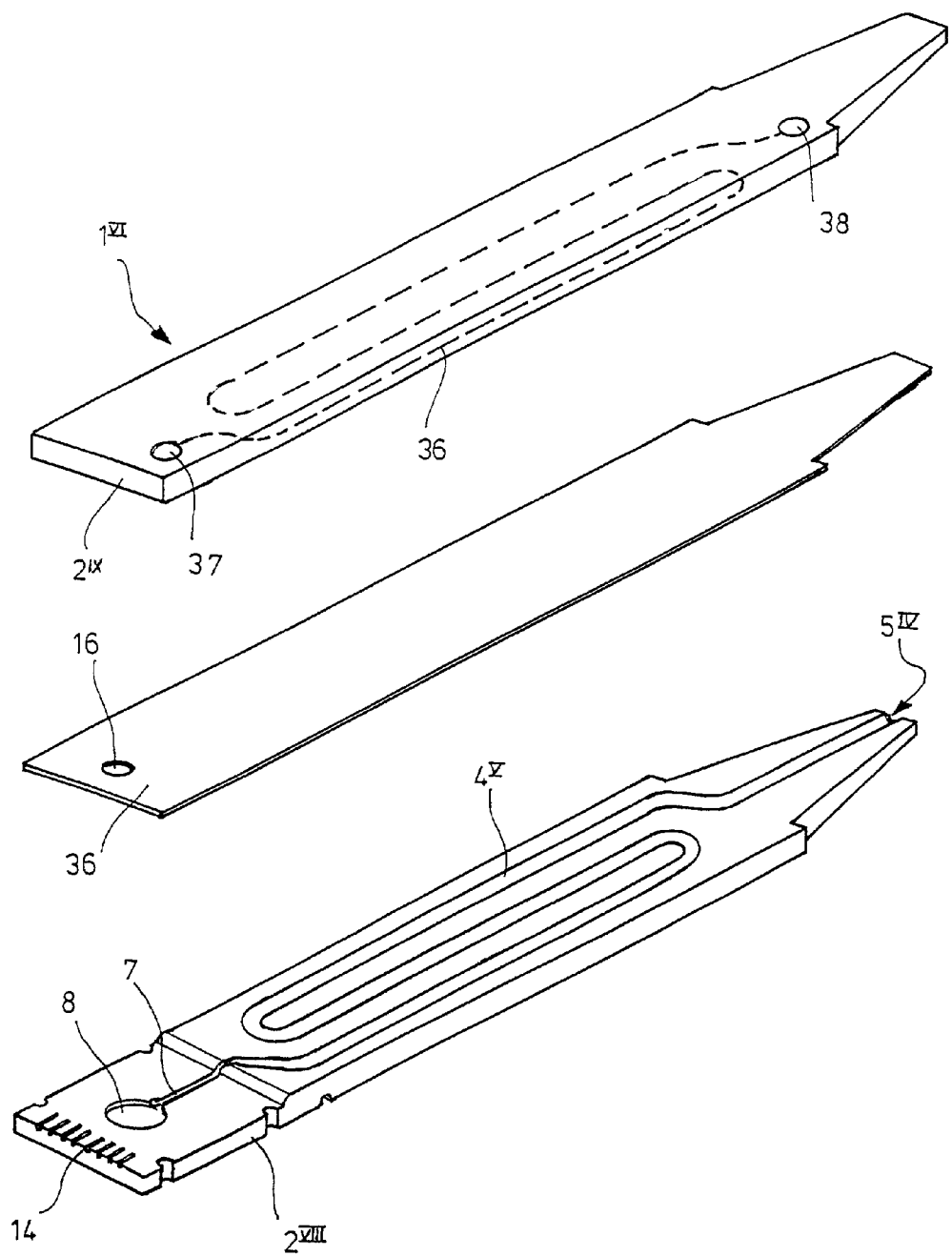
FIG. 16 FIG. 16 shows a dialytical disposable in an exploded perspective view.

A membrane sheeting which is fixed by lamination or is otherwise mounted makes it easy to carry out different functions of a disposable. According to FIG. 16, arranging a dialytical membrane 36 between a lower volume-receiving part $2^{VIII}$ and an upper volume-receiving part $2^{IX}$ allows to create a dialytical disposable $1^{VI}$. The lower volume-receiving part $2^{VIII}$ has a well $4^V$, which runs in a meander shape from a mouth $5^{IV}$ to the channel 7 leading to the secondary reception 8. The dialytical sheeting 36 has a passage 16 which is associated with the secondary well 8.

The second volume-receiving part $2^{IX}$ has a chamber 36 which faces the chamber $4^V$ and runs in the same meander shape. The two ends of the chamber 36 are connected to apertures 37, 38 in the outer surface of the volume-receiving part $2^{IX}$.

The volume-receiving part $2^{IX}$ is shorter than the volume-receiving part $2^{VIII}$ and the dialytical membrane 36 so that it does not cover the passage 16. The three elements $2^{VIII}$, 36, and $2^{IX}$ are superposed and connected to each other in the arrangement shown.

Sample liquid may be drawn into the well $4^V$ if a displacement device is connected to the passage 16. Then, a dialytical liquid may be flushed through the chamber 36 through the apertures 37 and 38. Thus, it is feasible to desalt a sample liquid by using a low-salt dialytical solution.

The scope of the invention makes it possible to design disposables of any type with two planar parts or volume-receiving parts which are interconnected via a joint (e.g. a film hinge) so that they can be processed together and can be superposed merely by folding them together.

Figures 17, 18:
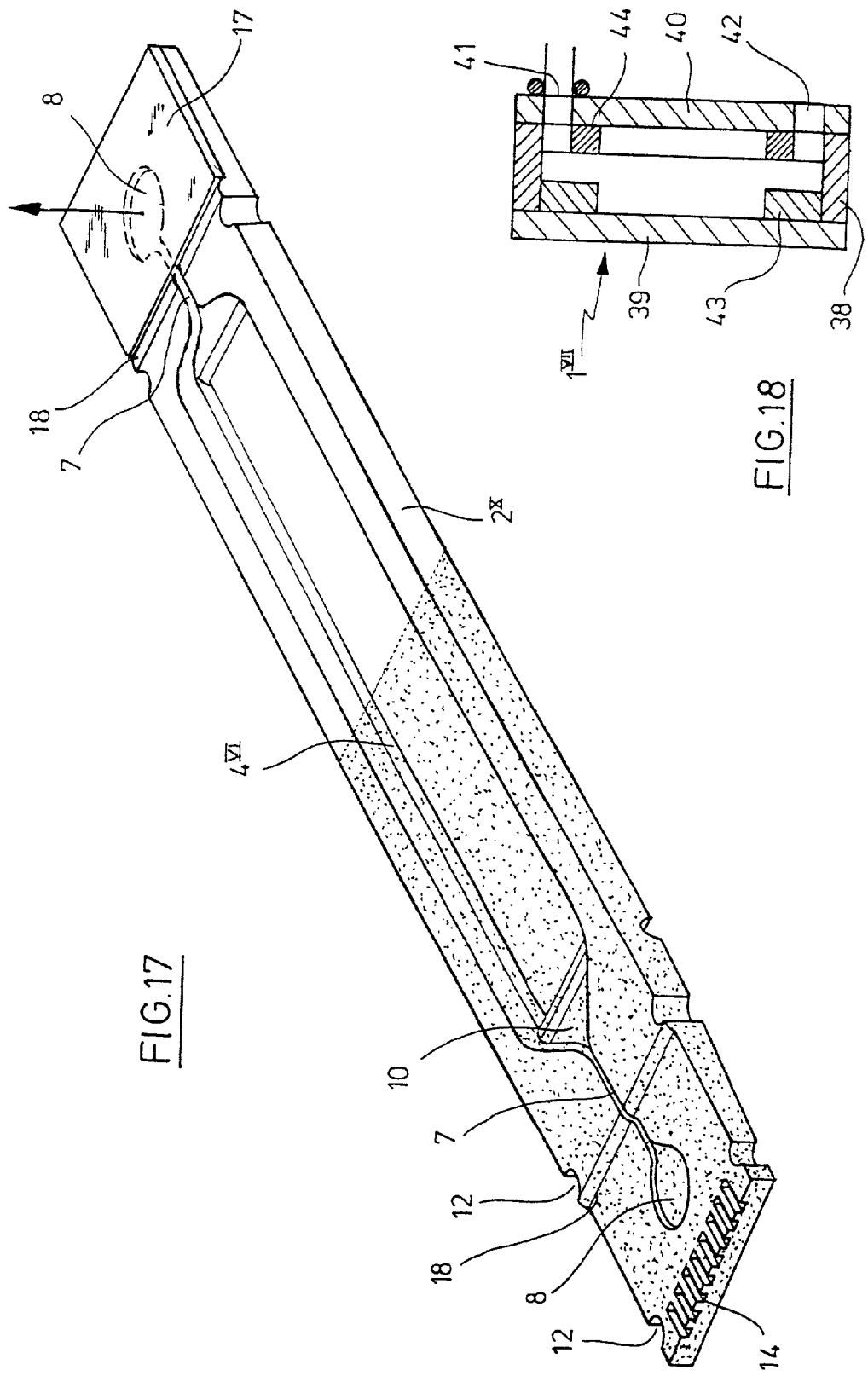
FIG. 17 shows the volume-receiving part of a centrifuging/filtration disposable in a perspective plan view.
FIG. 18 shows a cuvette disposable in a perspective longitudinal section.

FIG. 17 shows a volume-receiving part $2^X$ of a centrifuging/filtration disposable. It is composed of two halves which are arranged in a specular symmetry with respect to a transverse middle plane and one of which is tinted dark and the other of which is tinted bright in the drawing for reasons of clarity. The two halves correspond to the half which is the left-hand one of the volume-receiving part 2 of FIG. 1 in the drawing.

Thus, the well $4^{VI}$ is connected to secondary wells 8 via channels 7 at the two ends.

The shoulder 18 of the half which is on the right in the drawing has mounted thereon a membrane 17 (e.g. an ultra-filtration membrane) which has a separating function.

The whole is additionally covered by a cover sheeting which has passages in the area of the secondary wells 8.

The sample is received through the secondary well 8 which is on the left in the drawing and the filtrate is withdrawn through the secondary well 8 which is on the right in the drawing. The retained substance is left behind in front of the membrane 17.

The reception of the sample liquid and its separation into a filtrate and a retained substance are effected by applying a negative pressure and/or by using the centrifugal force.

Finally, FIG. 18 shows a cuvette disposable $1^{VII}$ in a roughly schematic way. It has a planar framework part 38 which, on either side, is coated with PFA sheetings 39, 40 a property of which is permeability to ultraviolet radiation. The sheeting 14 has apertures 41 and 42 to pass through a sample liquid or displacement air. The insides of the sheetings have seated thereon frame-shaped elements 43, 44 which serve for supporting the sheeting 39, 40 and for flow guidance.

What is claimed is:

1. A system for handling liquid samples, comprising:
at least one device for handling liquid samples (1)
having at least two superposed and interconnected planar elements (2, 3) between which a well (4) for a liquid sample is formed which extends between an outwardly leading mouth (5) to receive and deliver a liquid sample and an outwardly leading passage (16) to connect the well (4) to a displacement device (21) for air or another gas; and
a handling apparatus having a displacement device (21), a device for releasably mounting the at least one device for handling the liquid samples (1), and a line (20) sealingly connecting the displacement device (21) to the passage (16) if the device for handling liquid samples (1) is disposed in the device for releasably mounting,
wherein the mouth (5) of the device for handling liquid samples (1) is disposed in a first peripheral area or in the vicinity thereof, and the passage (16) is disposed in the vicinity of a second peripheral area remote from the first peripheral area or in this second peripheral area, wherein the at least one device for handling liquid samples (1) is substantially of a tongue shape with a tapered end and has the mouth (5) in a first end side and the passage (16) in a longitudinal side, and wherein the at least one device for handling liquid samples (1) is tapered towards the mouth (5) in the main plane of extension of the planar elements (2, 3) and/or in a direction perpendicular thereto.

2. The system according to claim 1, wherein the planar elements (2, 3) and/or the limitation wall of the device for handling liquid samples (1) are laminas and/or sheetings and/or membranes.

3. The system according to claim 1, wherein the planar elements (2, 3) of the device for handling liquid samples (1) are made of plastic and/or glass and/or a semiconductor material and/or metal.

4. The system according to claim 1, wherein the well (4) of the device for handling liquid samples (1) comprises an indentation in one side of a planar element (2) which is covered by another planar element (3) and/or wherein the well (4) comprises indentations in the sides facing each other of two superposed planar elements (2, 3) and/or wherein the well (4) comprises a through opening in a planar element (2, 3) which is covered by planar elements (2, 3) on either side.

5. The system according to claim 4, wherein a planar element (2) of the device for handling liquid samples (1) covers a lamina having a well formed as an indentation on one side and another planar element (3) is a sheeting which covers the lamina on the side where the well (4) is.

6. The system according to claim 1, wherein the mouth (5) of the device for handling liquid samples (1) is extended outwardly in a first peripheral area of the interconnected planar elements (2, 3) between the interconnected planar elements (2, 3) or is extended outwardly in a cross direction through one of the interconnected planar elements (2, 3).

7. The system according to claim 1, wherein the passage (16) of the device for handling liquid samples (1) is extended outwardly in a cross direction through one of the interconnected planar elements (2, 3) or is extended outwardly in a second peripheral area of the interconnected planar elements (2, 3) between the interconnected planar elements (2, 3).

8. The system according to claim 6, wherein the mouth (5) of the device for handling liquid samples (1) is extended outwardly between a lamina and a sheeting and/or the passage (16) is extended outwardly in a cross direction through a sheeting covering a lamina.

9. The system according to claim 1, wherein the well (4) of the device for handling liquid samples (1) is a channel.

10. The system according to claim 1, wherein the mouth (5) of the device for handling liquid samples (1) is disposed at one end of the well (4) and the passage (16) is disposed at the other end of the well (4).

11. The system according to claim 9, wherein the channel substantially extends in the longitudinal direction of the device for handling liquid samples (1).

12. The system according to claim 9, wherein the channel of the device for handling liquid samples (1) is of a meander shape or a spiral shape.

13. The system according to claim 1, wherein the well (4) of the device for handling liquid samples (1), at its end opposed to the mouth (5), is connected to a secondary well (8), which is smaller than the well (4), via a channel having a cross-section which is smaller than that of the well (4).

14. The system according to claim 1, wherein the well (4) of the device for handling liquid samples (1) is tapered towards the mouth (5) in a nozzle-like manner and/or is expanded in a diffusor-like manner.

15. The system according to claims 1, wherein the mouth (5) of the device for handling liquid samples (1) comprises a plurality of mouth channels which are oriented in parallel or towards a common centre or are divergent.

16. The system according to claim 1, wherein the device for handling liquid samples (1), in the vicinity of the mouth (5), has at least one step (35) and/or at least one guide element in order to be supported and/or guided on a reference object.

17. The system according to claim 1, wherein the device for handling liquid samples (1), outside around the border of the passage (16), has a sealing surface to sealingly connect a displacement device (21) there.

18. The system according to of claim 1, wherein the well (4) of the device for handling liquid samples (1) has a plurality of reception chambers ($4^{IV}$) which are connected to each other by connection channels (33).

19. The system according to claim 1, wherein at least one planar element (2, 3) of the device for handling liquid samples (1) has a surface adjacent to the well (4) that is chemically modified and/or is structured.

20. The system according to claim 1, wherein the device for handling liquid samples (1) has at least one additional functional element which is a membrane (17) and/or a nonwoven fabric and/or a filtration element and/or an optical window and/or an electrode and/or a surface-enlarging and/or turbulence-promoting and/or shear force-producing structure and/or is a positioning element and/or a catch member and/or a code (14).

21. The system according to claim 20, wherein the membrane (17) and/or the nonwoven fabric and/or the filtration element of the device for handling liquid samples (1) is disposed between two planar elements (2, 3) between a well (4) and a passage (16) and/or at least two wells (4) and/or one well (4) and a mouth (5) of the various planar elements (2, 3).

22. The system according to claim 21, wherein a planar element (2) of the device for handling liquid samples (1) has at least one indentation (18) in which the membrane (17) and/or the nonwoven fabric and/or the filtration element are placed so that it/they forms/form a plane, which is completely covered by another planar element (3), with the adjacent area of the planar element (2).

23. The system according to claim 24, wherein the well (4V) for a sample liquid of the device for handling liquid samples (1), in a planar element, have associated therewith a well (36) for a dialytic liquid in a further planar element and the two wells (4V, 36) are separated by a dialytic membrane (36') disposed between the planar elements.

24. The system according to claim 23, wherein the well (36) of the device for handling liquid samples (1) for a dialytic liquid has at least one aperture (37, 38) to pass a dialytic liquid therethrough.

25. The system according to claim 20, wherein the code (14) and/or the positioning element and/or the catch element, at an outside of the device for handling liquid samples (1), are disposed at a spacing from the mouth (5).

26. The system according to claim 1, wherein at least one planar element (2, 3) of the device for handling liquid samples (1) is permeable to radiation for an optical measurement.

27. The system according to claim 1, wherein the device for handling liquid samples (1) has at least one light beam-conducting element for an optical measurement.

28. The system according to claim 1, wherein the mouth (5) and/or the passage (16) and/or the aperture (37, 38) of the device for handling liquid samples (1) have associated therewith at least one closure which can be optionally closed.

29. A system having a plurality of juxtaposed and interconnected devices of the device for handling liquid samples (1) according to claim 1.

30. The system according to claim 29, wherein the plurality of juxtaposed and interconnected devices of the device for handling liquid samples (1) are formed from common planar elements (2, 3).

31. A system comprising a plurality of superposed devices for handling liquid samples (1) according to claim 1.

32. The system according to claim 31, wherein the superposed devices for handling liquid samples (1) are connected to each other.

33. The system according to claim 29, wherein the device for handling liquid samples (1) is adapted to be disassembled into at least two smaller devices for handling liquid samples (1) along at least one break line disposed between two wells.

34. The system according to claim 1, wherein the displacement device (21) or the actuation device and the device for mounting are fixedly connected to each other.

35. The system according to claim 1, wherein the displacement device (21) has at least one piston cylinder device (24, 25).

36. The system according to claim 1, wherein the displacement device (21) has a pump and a valve device to connect or disconnect the suction end in the pump to or from the device for handling liquid samples (1).

37. The system according to claim 36, which has a chamber for a positive and/or negative pressure which is connected to the pump and is adapted to be connected to the device for handling liquid samples via the valve device.

38. The system according to claim 1, wherein the displacement device (21) or the actuation device initiates one or more pressure fluctuations in the well (4) in a mixed mode of operation in order to thoroughly mix a liquid sample in the well (4).

39. The system according to claim 1, wherein the device for releasably mounting is a plug-in well into which a device for handling liquid samples (1) is adapted to be lockingly plugged in with a plug-in end.

40. The system according to of claim 1, wherein the device for releasably mounting has associated therewith a pressure spring (23) which presses a plugged-in device for handling liquid samples (1) against the line (20) or the actuation device.

41. The system according to claim 1, wherein the line (20) has associated therewith an O-type sealing ring (22) for sealingly bearing on the outer edge of the passage (16) of the device for handling liquid samples (1).

42. The system according to claim 1, wherein the device for releasably mounting helps in mounting at least two devices for handling liquid samples (1) in such a way that the wells (4) thereof are sealingly connected to each other via the passage (16) and/or the mouth (5) and the passage (16) or the limitation wall of one device for handling liquid samples (1) is connected to the displacement device (21) or is coupled to the actuation device in order to receive a sample liquid in a device for handling liquid samples (1) from outside and/or to deliver it to the outside and/or to transfer it between at least two devices for handling liquid samples.

43. The system for handling liquid samples according to claim 1, comprising a handling apparatus with a centrifuge rotor (27) which has a device for releasably mounting at least one device for handling liquid samples (1).

44. The system according to claim 43, wherein the device for releasably mounting is a well (28) for positively receiving a device for handling liquid samples (1).

45. The system according to claim 43, wherein the well has recessed grips (29) for laterally gripping the device for handling (1) and/or has locking elements for laterally locking the device for handling liquid samples (1) in place and/or has sealing elements for sealing the apertures of the device for handling (1).

46. The system according to claim 1, which has a device for releasably mounting at least two devices for handling liquid samples (1) which is such that the wells (4) thereof are sealingly connected to each other via the passage (16) and/or the mouth (5) in order to transfer sample liquid between the devices for handling liquid samples (1) during centrifuging.

47. A system for handling liquid samples according to claim 1, including a handling apparatus with a heating device and a support associated therewith for storing at least one device for handling liquid samples (1) so that a liquid sample received therefrom is adapted to be heated by means of the heating device.

48. The system according to claim 47, wherein the heating device has a contact surface which comes into a surface contact with a planar element (2,3) of the device for handling liquid samples (1) if a device for handling liquid samples (1) is stored on the support.

49. A system for handling liquid samples according to claim 1, including a handling apparatus with an optical measuring device and a device for releasably mounting at least one device for handling liquid samples (1) so that the latter, if arranged in the device for releasably mounting, is disposed with its well (4) in the path of beams of the optical measuring device.

50. The system according to claim 1, wherein the elements of one or more handling apparatuses are disposed in or on at least one chassis and/or casing.

51. The system according to claim 50, wherein a plurality of handling apparatuses have one or more common elements.

52. The system according to claim 1, wherein the at least one handling apparatus is manually operable and/or works automatically and/or is an apparatus that can be held by hand (a hand-operated apparatus).

53. The system according to claim 1, wherein at least two handling apparatuses interact automatically.

54. The system according to claim 1, wherein at least one further handling device exists for transporting devices for handling liquid samples (1) between various handling apparatuses and/or at least one handling apparatus and an input station and/or an output station and/or for supporting the handling apparatuses during their operation.

* * * * *